United States Patent
Viswanathan et al.

(10) Patent No.: US 9,676,837 B2
(45) Date of Patent: Jun. 13, 2017

(54) COLLAGEN 7 AND RELATED METHODS

(75) Inventors: Malini Viswanathan, Action, MA (US); Mark DeSouza, Boston, MA (US)

(73) Assignee: Shire Human Genetic Therapies, Inc., Lexington, MA (US)

( * ) Notice: Subject to any disclaimer, the term of this patent is extended or adjusted under 35 U.S.C. 154(b) by 22 days.

(21) Appl. No.: 14/236,403

(22) PCT Filed: Aug. 3, 2012

(86) PCT No.: PCT/US2012/049553
§ 371 (c)(1),
(2), (4) Date: Sep. 12, 2014

(87) PCT Pub. No.: WO2013/020064
PCT Pub. Date: Feb. 7, 2013

(65) Prior Publication Data
US 2015/0011733 A1 Jan. 8, 2015

Related U.S. Application Data

(60) Provisional application No. 61/514,796, filed on Aug. 3, 2011.

(51) Int. Cl.
| | | |
|---|---|---|
| *C07K 14/78* | (2006.01) | |
| *C12P 21/02* | (2006.01) | |
| *C12N 9/10* | (2006.01) | |
| *A61K 38/00* | (2006.01) | |
| *C12N 9/02* | (2006.01) | |
| *C12N 9/48* | (2006.01) | |
| *C12N 15/85* | (2006.01) | |

(52) U.S. Cl.
CPC ............ *C07K 14/78* (2013.01); *C12N 9/1048* (2013.01); *C12P 21/02* (2013.01); *C12Y 304/13009* (2013.01); *A61K 38/00* (2013.01); *C12N 9/0071* (2013.01); *C12N 9/1081* (2013.01); *C12N 9/485* (2013.01); *C12N 15/85* (2013.01); *C12N 2800/22* (2013.01); *C12Y 114/11002* (2013.01)

(58) Field of Classification Search
None
See application file for complete search history.

(56) References Cited

U.S. PATENT DOCUMENTS

| | | |
|---|---|---|
| 2002/0142391 A1 | 10/2002 | Kivirikko et al. |
| 2003/0138822 A1 | 7/2003 | Glenn et al. |
| 2005/0229264 A1 | 10/2005 | Chang et al. |
| 2007/0105122 A1 | 5/2007 | Ota et al. |

FOREIGN PATENT DOCUMENTS

| | | |
|---|---|---|
| EP | 2330112 A1 | 6/2011 |
| JP | 2003-513988 A | 4/2003 |
| WO | 0134801 A2 | 5/2001 |
| WO | 2012/149136 A1 | 11/2012 |

OTHER PUBLICATIONS

Christiano et al., "Cloning of Human Type VII Collagen", 1994, vol. 269, No. 32, pp. 20256-20262.*
Gustafsson et al., "Codon bias and heterologous protein expression", TRENDS in Biotechnology, 2004, vol. 22 No. 7, 346-353.*
Mei Chen et al., "The Recombinant Expression of Full-length Type VII Collagen and Characterization of Molecular Mechanisms Underlying Dystrophic Epidermolysis Bullosa", The Journal of Biological Chemistry, vol. 277, No. 3, Jan. 18, 2002, pp. 2118-2124.
Wojciech Miltyk et al., "Prolidase Dependent Inhibition of Collagen Biosynthesis in Chinese Hamster Ovary Cells", J. Biochem., vol. 144, 2008, pp. 409-414.
Partial Supplementary European Search Report dated Feb. 12, 2015, European Application No. 12820654.7, pp. 1-8.
First Office Action dated Mar. 31, 2015, Chinese Application No. 201280047084.3, pp. 1-16.
International Search Report dated Nov. 2, 2012, International Application No. PCT/US2012/49553, pp. 1-3.
Extended European Search Report dated Jun. 9, 2015, European Application No. 12820654.7, pp. 1-10.
Australian Office Action dated Sep. 29, 2016 for Australian Patent Application No. 2012289916, 7 Pages.
M. Levine, "Topics in Dental Biochemistry", Springer Science and Business Media, 2010, ISBN 3540881166, pp. 1-307.
Japanese Office Action dated Jun. 14, 2016 for Japanese Patent Application No. 2014-524112, Original and English Translation, 12 Pages.
Bragonzi et al., "A new Chinese hamster ovary cell line expressing α2, 6-sialyltransferase used as universal host for the production of human-like sialylated recombinant glycoproteins", Biochimica el Biophysica Acta, vol. 1474, No. 3, 2000, pp. 273-282.
Chinese Notification of Reexamination dated Mar. 22, 2017 for Chinese Patent Application No. 201280047084.3, 7 pages.
Wang Kun, Practical Diagnostic Enzymology, Second Edition, 2000, p. 483.

* cited by examiner

*Primary Examiner* — Suzanne M Noakes
(74) *Attorney, Agent, or Firm* — MH2 Technology Law Group, LLP

(57) ABSTRACT

Disclosed are methods of making collagen 7, or functional fragments thereof, as well as collagen 7, and functional fragments thereof produced by such methods, nucleic acids encoding collagen 7, and functional fragments thereof, as well as vectors and host cells comprising such nucleic acids.

15 Claims, No Drawings

COLLAGEN 7 AND RELATED METHODS

This application is the U.S. National Phase Application under 35 U.S.C. §371 of International Application No. PCT/US2012/049553, filed Aug. 3, 2013, which claims priority to U.S. provisional application 61/514,796, filed Aug. 3, 2012. These prior applications are incorporated by reference herein in their entirety.

The invention relates to collagen 7, collagen 7 related nucleic acids and cells, and related methods.

BACKGROUND

Collagens are a family of proteins that strengthen and support connective tissues, such as the skin, tendons, ligaments, and bones. Collagen 7, as the major component of anchoring fibrils, functions in strengthening and stabilizing various tissues, including the skin (Ricard-Blum, *Cold Spring Harb Perspect Biol* 3(1):a004978 (2011)).

Collagen 7 is synthesized as three pro-α1(VII) polypeptide chains, which are subsequently processed and folded into a triple helical procollagen 7 protein in the endoplasmic reticulum. Procollagen 7 is secreted into the extracellular space, where it is further processed into mature collagen 7 (Chung et al. *Dermatol Clin* 28(1): 93-105 (2010)). Mature collagen 7 undergoes a multistep polymerization process to form the structural anchoring fibrils (Fritsch et al. *J Biol Chem* 284(44): 30248-30256 (2009)). In the skin, these anchoring fibrils are found in the epidermal basement membrane zone, which is the two-layer membrane located between the top layer of skin, the epidermis, and the underlying dermis. Here the anchoring fibrils connect the epidermal basement membrane to the papillary dermis. This connection aids in holding the epidermal and dermal layers of the skin together, providing structure and stability to the skin (Villone et al. *J Biol Chem* 283(36): 24506-24513 (2008)).

SUMMARY OF THE INVENTION

In one aspect, the disclosure features, a method of making collagen 7, or a functional fragment thereof. The method comprises:

providing a cell, e.g., a mammalian cell, e.g., a CHO or HEK cell, genetically modified to express collagen 7, or a functional fragment thereof, and, optionally, one or more polypeptides, e.g., one or more polypeptides that increase collagen 7 production in the cell (e.g., prolidase and/or prolyl hydroxylase); and culturing the cell under conditions sufficient for the production of collagen 7, or functional fragment thereof, thereby making collagen 7, or a functional fragment thereof.

In one embodiment, the collagen 7 is human collagen 7. In an embodiment, the collagen 7 is encoded by a high glycine codon optimized sequence, e.g., a high glycine codon optimized sequence described herein. In one embodiment, the collagen 7 has the amino acid sequence of SEQ ID NO 2. In one embodiment, the amino acid sequence of the collagen 7 is at least 80, 90, 95, or 99% identical to SEQ ID NO 2. In one embodiment, the amino acid sequence of collagen 7 differs from SEQ ID NO 2 by no more than 1, 2, 3, 4, 5, 6, 7, 8, 9, 10, 15 or 20 amino acid residues.

In an embodiment, the cell is genetically modified to express prolidase, or a functional fragment thereof, and, e.g., the prolidase can be a mammalian, e.g., a human prolidase, or a rodent, e.g., mouse, rat or hamster prolidase. In an embodiment the prolidase is: human prolidase, e.g., human prolidase having the amino acid sequence of SEQ ID NO 4; prolidase having an amino acid sequence at least 80, 90, 95, or 99% identical with SEQ ID NO 4; prolidase having an amino acid sequence that differs from SEQ ID NO 4 by no more than 1, 2, 3, 4, 5, 6, 7, 8, 9, 10, 15 or 20 residues.

In an embodiment, the cell is genetically modified to express prolyl hydroxylase, or a functional fragment thereof, and, e.g., the prolyl hydroxylase can be a mammalian, e.g., a human prolyl hydroxylase, or a rodent, e.g., mouse, rat or hamster prolyl hydroxylase. In an embodiment the prolyl hydroxylase is: human prolyl hydroxylase, e.g., human prolyl hydroxylase having the amino acid sequence of SEQ ID NO 6; prolyl hydroxylase having an amino acid sequence at least 80, 90, 95, or 99% identical with SEQ ID NO 6; prolyl hydroxylase having an amino acid sequence that differs from SEQ ID NO 6 by no more than 1, 2, 3, 4, 5, 6, 7, 8, 9, 10, 15 or 20 residues.

In an embodiment, the cell is genetically modified to express a glycosyl transferase, or functional fragment thereof, e.g., a sialyltransferase, or functional fragment thereof. The glycosyl transferase can be a mammalian, e.g., a human glycosyl transferase, e.g., sialyltransferase, or a rodent, e.g., mouse, rat or hamster glycosyl transferase.

In an embodiment, the glycosyl transferase is a sialyltransferase, e.g., a sialyltransferase having the amino acid sequence of SEQ ID NO 5; a sialyltransferase having an amino acid sequence at least 80, 90, 95, or 99% identical to SEQ ID NO 5; a sialyltransferase having an amino acid sequence that differs from SEQ ID NO 5 at no more than 1, 2, 3, 4, 5, 6, 7, 8, 9, 10, 15 or 20 residues.

In an embodiment, the genetically modified cell comprises a nucleic acid that encodes collagen 7, or a functional fragment thereof, e.g., a high glycine codon optimized nucleic acid sequence, e.g., a nucleic acid sequence of SEQ ID NO 1. In one embodiment, the nucleic acid sequence is at least 80, 90, 95, or 99% identical to SEQ ID NO 1; the nucleic acid sequence differs from SEQ ID NO 1 at no more than 1, 2, 3, 4, 5, 6, 7, 8, 9, 10, 15 or 20 nucleotides. In an embodiment, at least 80, 90, 95, or 99% of the codons have the codon value of SEQ ID NO 1.

In an embodiment the genetically modified cell comprises a nucleic acid that encodes a prolidase, or functional fragment thereof.

In an embodiment the genetically modified cell comprises a nucleic acid that encodes a prolyl hydroxylase, or functional fragment thereof.

In an embodiment the genetically modified cell comprises a nucleic acid that encodes a glycosyl transferase, or functional fragment thereof.

In an embodiment, the cell comprises an expression vector that comprises a nucleic acid sequence that encodes collagen 7, or a functional fragment thereof. In an embodiment said expression vector further comprises a nucleic acid sequence that encodes prolidase, or a functional fragment thereof. In an embodiment said expression vector further comprises a nucleic acid sequence that encodes prolyl hydroxylase, or a functional fragment thereof. In an embodiment, said expression vector further comprises a nucleic acid sequence that encodes glycosyl transferase, or a functional fragment thereof. In an embodiment, said expression vector further comprises a nucleic acid sequence that encodes prolidase, or a functional fragment thereof, and a nucleic acid sequence that encodes glycosyl transferase, or a functional fragment thereof. In an embodiment, said expression vector further comprises a nucleic acid sequence that encodes prolyl hydroxylase, or a functional fragment thereof, and a nucleic acid sequence that encodes glycosyl transferase, or a functional fragment thereof.

In an embodiment, the cell comprises a second expression vector that comprises a nucleic acid sequence that encodes prolidase, or a functional fragment thereof.

In an embodiment, the cell comprises a second expression vector that comprises a nucleic acid sequence that encodes prolyl hydroxylase, or a functional fragment thereof.

In an embodiment, the cell comprises a third expression vector that comprises a nucleic acid sequence that encodes glycosyl transferase, or a functional fragment thereof.

In an embodiment, the cell comprises a second expression vector that comprises a nucleic acid sequence that encodes prolidase, or a functional fragment thereof, and a third expression vector that comprises a nucleic acid sequence that encodes glycosyl transferase, or a functional fragment thereof.

In an embodiment, the cell comprises a second expression vector that comprises a nucleic acid sequence that encodes prolyl hydroxylase, or a functional fragment thereof, and a third expression vector that comprises a nucleic acid sequence that encodes glycosyl transferase, or a functional fragment thereof.

In an embodiment, the cell is a mammalian cell, e.g., a human, or rodent, e.g., a rat, mouse or Chinese hamster cell.

In an embodiment, the cell is a CHO cell.

In an embodiment, the cell is a HEK293 cell.

In an embodiment, the method further comprising recovering collagen 7, or the functional fragment thereof, from said cultured cell.

In an embodiment, the collagen 7, or functional fragment thereof, is recovered from culture medium.

In an embodiment, the method further comprises purifying collagen 7, or functional fragment thereof, from said cultured cell.

In an embodiment, the method further comprising purifying collagen 7, or functional fragment thereof, from culture medium.

In an embodiment, at least 30, 40, 50, 60, 70, 80, 90 or 95% of said collagen 7, or functional fragment thereof, is incorporated into homotrimers.

In an embodiment, at least 30, 40, 50, 60, 70, 80, 90 or 95% of said collagen 7, or functional fragment thereof, is incorporated into hexamers.

In another aspect, the disclosure features, a vector described herein.

In another aspect, the disclosure features, a cell, or isolated preparation of cells, described herein.

In another aspect, the disclosure features, a high glycine optimized sequence encoding collagen 7 described herein.

In another aspect, the disclosure features an isolated preparation of cells described herein which can further comprise any of culture medium, and collagen 7, or functional fragment thereof, produce by said cell.

In another aspect, the disclosure features, a method of making a cell suitable for expressing collagen 7, or functional fragment thereof, comprising:

recombinantly manipulating a cell, e.g., a mammalian cell, e.g., a mammalian cell described herein, to express recombinant collagen 7, or functional fragment thereof; and optionally, recombinantly manipulating said cell to express one or more polypeptides, e.g., one or more polypeptides that increase collagen 7 production in the cell (e.g., prolidase and/or prolyl hydroxylase);

thereby making a cell suitable for expressing recombinant collagen 7.

In one embodiment, the method comprises recombinantly manipulating a cell to express a collagen 7 encoded by a high glycine codon optimized nucleic acid sequence, e.g., a high glycine codon optimized nucleic acid sequence described herein.

In an embodiment of the method, the cell is recombinantly manipulated to express collagen 7, or a functional fragment thereof, and the cell is recombinantly manipulated to express one or more polypeptides, e.g., that increase the expression of collagen 7 in the cell. In one embodiment, the cell is recombinantly manipulated to express collagen 7, or a functional fragment thereof before said cell is recombinantly manipulated to express one or more polypeptides, e.g., that increase the expression of collagen 7 in the cell, e.g., one or more of prolidase, prolyl hydroxylase, glycosyl transferase, and functional fragments thereof.

In one embodiment, the cell is recombinantly manipulated to express collagen 7, or a functional fragment thereof after said cell is recombinantly manipulated to express one or more polypeptides, e.g., that increase the expression of collagen 7 in the cell, e.g., one or more of prolidase, prolyl hydroxylase, glycosyl transferase, and functional fragments thereof.

In an embodiment of the method, the cell is recombinantly manipulated to express collagen 7, or a functional fragment thereof, at the same time said cell is recombinantly manipulated to express one or more polypeptides, e.g., that increase the expression of collagen 7 in the cell, e.g., one or more of prolidase, prolyl hydroxylase, glycosyl transferase, and functional fragments thereof.

In another aspect, the invention features, collagen 7, or a functional fragment thereof, made by a method described herein.

In another aspect, the invention features, a purified or isolated preparation of collagen 7, or functional fragment thereof, made by a method described herein.

In another aspect, the invention features, a purified or isolated preparation of collagen 7, or functional fragment thereof, wherein at least 30, 40, 50, 60, 70, 80, 90 or 95% of said collagen 7, or functional fragment thereof, is incorporated into homotrimers.

In another aspect, the invention features, a purified or isolated preparation of collagen 7, or a functional fragment thereof, wherein at least 30, 40, 50, 60, 70, 80, 90 or 95% of said collagen 7, or functional fragment thereof, is incorporated into hexamers.

In another aspect, the invention features, a method of purifying collagen 7, or a functional fragment thereof, comprising:

providing conditioned cell medium, e.g., from culture of a cell described herein;

subjecting the collagen 7, or functional fragment thereof, from said medium to an anion exchange chromatography, e.g., with Q sepharose;

thereby purifying collagen 7, or a functional fragment thereof.

In an embodiment, the method comprises:

providing conditioned cell medium, e.g., from culture of a cell described herein;

optionally, precipitating protein, e.g., with ammonium sulfate, to form precipitated protein;

solubilizing the precipitated protein to form solubilized protein;

dialyzing the solubilized protein to form dialysate;

segmenting the dialyzed sample to form a supernatant; and subjecting the supernatant to an anion exchange chromatography, e.g., with Q sepharose;
thereby purifying collagen 7, or functional fragment thereof.

The details of one or more embodiments of the invention are set forth in the description below. Other features, objects, and advantages of the invention will be apparent from the description and the drawings, and from the claims.

DETAILED DESCRIPTION

Definitions

"Recombinantly manipulated to express" or "genetically manipulated to express", as used herein, refers to a cell which has been modified so as to express a protein. Exemplary modifications include, the introduction of a nucleic acid which encodes the protein, or the placement of an endogenous sequence encoding the protein under control of a sequence other than the native endogenous sequence, e.g., by introduction of a sequence that activates an endogenous gene.

Isolated nucleic acid molecules, as used herein, means the nucleic acids have been separated from the nucleic acids of the genomic DNA or cellular RNA of their source origin. This includes nucleic acid molecules obtained by suitable methods, including, but not limited to, chemical methods, combinations of chemical and biological methods, and isolated recombinant nucleic acid molecules.

Recombinant, as used herein, in reference to a nucleic acid molecule, pertains to nucleic acid molecules which have been engineered using molecular biological techniques. Recombinant, as used herein, in reference to a protein or polypeptide molecule, pertains to a protein or polypeptide molecule expressed utilizing isolated nucleic acid molecules or recombinant nucleic acid molecules.

High glycine optimized or high glycine codon optimized, as used herein, refers to a nucleic acid sequence that encodes collagen 7, or a functional fragment thereof. The sequence includes at least one glycine codon that is other than the most common glycine codon, which is referred to herein as a less common codon. In an embodiment, the less common glycine codon is other than the most common glycine codon for the cell in which the sequence will be expressed. By way of example, if the sequence is to be expressed in CHO cells, the less common glycine codon is other than the most common glycine codon in CHO cells. In an embodiment, the less common glycine codon is a less common glycine codon for a cell referred to herein, e.g., a CHO or HEK cell. In embodiments, the sequence includes at least one, and in embodiments, at least 10, 20 or 30, less common glycine codons that is not present in the native human sequence for collagen 7. In an embodiment at least 10, 20, 30, 40, 50, 60, 70, 80, 90, or 100% of the glycine codons are less common glycine codons.

Collagen 7

As a major component of anchoring fibrils, collagen 7 functions in maintaining tissue integrity. Anchoring fibrils are structural elements that serve as attachment complexes at the interface between the epithelial and mesenchymal layers of several tissues, including the skin, oral mucosa, and cervix (Chung et al. *Dermatol Clin* 28(1): 93-105 (2010)). In the skin, anchoring fibrils extend from the lower portion of the epidermal basement membrane to the underlying papillary dermis, securing the association between the epidermal basement membrane and the papillary dermis (Varki et al. *J Med Genet* 44:181-192 (2007)). This association aids to provide and maintain cohesion between the epidermis and dermis, contributing to the integrity to the skin, which is critical for its proper structure, function, and homeostasis (Villone et al. *J Biol Chem* 283(36): 24506-24513 (2008)).

Nucleic acids that encode collagen 7 can be used in the methods described herein. High glycine codon optimized sequences are particularly suitable. An exemplary high glycine codon optimized nucleotide sequence for human collagen 7 is as follows:

(SEQ ID NO: 1)
aagcttcgaagtttaaactgagtgccgccaccatgaccctg cggctgctggtggctgccctgtgtgctggcatcctggccga ggctcctagagtgcgggcccagcaccgcgagagagtgacct gcaccagactgtacgccgccgatatcgtgttcctgctggac ggctcctcctccatcggccggtccaacttcggggaagtgcg gtccttcctggaaggcctggtgctgcctttctccggcgctg cctctgcccagggcgtcagattcgccaccgtgcagtactcc gacgaccccggaccgagttcggcctggatgctctgggctc tggcggcgacgtgatccgggccatcagagagctgtcctaca agggcggcaacacccggacaggcgccgctatcctgcacgtg gccgaccatgtgtttctgccccagctggccagacccggcgt gcccaaagtgtgcatcctgatcaccgacggcaagtcccagg acctggtggacaccgccgctcagagactgaagggccagggc gtgaagctgttcgccgtgggcatcaagaacgccgacccga ggaactgaagcgggtggcctcccagcctacctccgatttct tcttcttcgtgaacgacttctccatcctgcggaccctgctg cccctggtgtctcggagagtgtgtaccaccgctggcggcgt gccagtgacccggcctcctgacgattctacctccgcccctc gggatctggtgctgtccgagccttccagccagtccctgaga gtgcagtggaccgccgcctctggccccgtgaccggctacaa ggtgcagtacacccctctgaccggcctgggccagcctctgc cttctgagcggcaagaagtgaacgtcccagccggcgagaca tccgtgcggctgagaggcctgaggcccctgaccgagtacca agtgaccgtgatcgccctgtacgccaacagcatcggcgagg ccgtgtccggcaccgccagaaccacagccctggaaggaccc gagctgaccatccagaacaccaccgcccactccctgctggt cgcttggagatctgtgcctggcgccaccggctatcgcgtga cctggcgagttctgtctggcggccctacccagcagcaagag ctgggccctggacagggctctgtgctgctgagggacctgga acccggcaccgactacgaagtgacagtgtccaccctgttcg gcagatccgtgggccctgccacctctctgatggccagaacc gacgcctccgtggaacagaccctgaggcctgtgatcctggg ccccaccagcatcctgctgagctggaacctggtgcccgagg ccagaggctaccggctggaatggcggagagagacaggcctg gaacctcccagaaggtggtcctgccctccgacgtgaccag -continued ataccagctggatggcctgcagcctggcaccgagtacagac
tgaccctgtacaccctgctcgagggcacgaggtggccacc
cctgctacagtggtgcctaccggccctgagctgcccgtgtc
ccctgtgaccgatctgcaggccaccgagctgcctggccagc
gcgtcagagtgtcttggtcccagtgccaggcgctacccag
taccggatcatcgtgcggtccacacagggcgtggaaagaac
cctggtgctccccggctcccagaccgccttcgacctggatg
atgtgcaggccggcctgagctacaccgtgcgggtgtccgct
agagtgggccctagagaaggctccgccagcgtgctgaccgt
gcgcagagagcctgaaaccctctggccgtgcccggactgc
gggtggtggtgtctgatgccaccagagtcagagtggcctgg
ggccctgtgccaggggcctccggcttcagaatctcctggtc
caccggctctggccctgagtcctctcagaccctgcccctg
actccaccgccaccgatatcaccggactgcagcccggaacc
acctaccaggtggccgtgtctgtgctgaggggcagagaaga
gggcccagccgccgtgatcgtggccaggacagatcctctgg
gcccagtgcggaccgtgcacgtgacccaggccagctccagc
tccgtgaccatcacctggaccagagtccctggcgctacagg
ctacagagtgtcctggcactctgcccacgcccccgagaagt
cccagctggtgtctggcgaggccaccgtggctgaactggac
ggcctcgagcccgacacagagtacacagtgcacgtgcgcgc
ccatgtggctggcgtggacggacctcctgcttccgtggtcg
tgcgcaccgctcctgagcccgtgggaagagtgtcccggctg
cagatcctgaacgcctccagcgacgtgctgcggatcacctg
ggtcggagtgaccggcgctaccgcttacagactggcttggg
gcagatctgagggcggaaccatgcggcatcagatcctgcct
ggcaacaccgactccgccgagatcagaggactggaaggcgg
cgtgtcctactctgtgcgcgtgaccgccctcgtgggcgaca
gagaaggcacccccgtgtccatcgtggtcaccaccccctcca
gaggcccctccagctctgggcaccctgcatgtggtgcagcg
gggcgagcactccctgagactgagatgggagcctgtgcctc
gggcccagggcttcctgctgcattggcagcctgaaggcggc
caagagcagtctagggtgctgggcccgagctgtccagcta
ccacctggacggactggaaccagccacccagtacagagtgc
ggctgtccgtgctgggacctgccggcgagggaccttctgcc
gaagtgaccgccaggaccgagtcccctcgggtgcctccat
cgagctgagagtggtggataccagcatcgacagcgtgaccc
tggcctggacccctgtgtcccgggcctcttcctacatcctg
tcttggaggcctctgaggggccaggccaagaggtgccagg
ctccccctcagacactgccaggcatcagctcctcccagcgcg -continued tgacaggactcgagcctggggtgtcctacatcttctccctg
acccccgtcctggacggcgtgcgcggacctgaggcttctgt
gacccagaccccagtgtgccccagaggcctggccgacgtgg
tctttctgcctcacgccacccaggacaacgcccacagagcc
gaggctaccagacgggtgctcgagagactggtgctggccct
gggaccactgggcccacaggctgtgcaagtgggcctgctgt
cttactcccaccggccctccccctgttcccctgaacggc
tctcacgacctgggcatcatcctgcagcggatccgggacat
gccctacatggaccctccggcaacaacctgggcaccgccg
tggtcacagcccaccggtacatgctggccccgatgctcct
ggcagacggcagcatgtccccggcgtgatggtgctgctcgt
ggacgagccctgcggggcgacatcttcagccctatcagag
aggcccaggctagcggcctgaacgtggtcatgctgggcatg
gctggcgccgaccctgagcagctgagaaggctggcccctgg
catggactccgtgcagaccttctttgccgtggacgacggcc
ccagcctggatcaggctgtgtctggcctggctaccgccctg
tgtcaggcctccttcaccacccagcccagacccgagccttg
ccccgtgtactgccctaagggccagaagggcgagcccggcg
agatgggcctgagaggacaagtgggacctccaggcgatccc
ggcctgcctggaagaacaggcgctcctggacctcagggccc
tcctggctctgctaccgctaagggcgagagaggcttcccag
gcgccgacggcagacctggctctccaggcagagccggcaat
cctggaacacctggcgccccaggcctgaagggatctcctgg
cttgcctggccctaggggcgaccctggcgaaagaggaccta
gaggccctaaaggcgagccaggcgcccctggccaagtgatc
ggcggagaaggacctggactgcccggcagaaagggcgatcc
tggcccttctggcccaccggcccaagaggtcctctgggag
atcctggaccaaggggcccaccaggcctgcccggaacagct
atgaagggcgataagggcgacaggggcgagcggggaccacc
aggaccaggcgaaggtggaatcgctcccggcgaacctgggc
tgccaggactgcctggatctcccggaccacagggacctgtg
ggcccacctggcaagaaggggggagaaaggcgactccgagga
cggggctccaggattgcccggccaaccaggctctcctggcg
aacagggtcccagaggacctcccggcgctatcggcccaaag
ggggacagaggattccctggcccactgggcgaggctggcga
aaaaggcgaacgcggaccccctggccctgccggcagtagag
gacttcctggcgttgccggcagaccaggcgccaagggacct
gaaggccctccaggccctaccggaaggcagggcgaaaaggg
ggaacctggcaggccaggcgacccagctgttgtgggaccag
ccgtggctggacccaaaggcgagaaaggggatgtgggaccc

```
gctgggcctagaggcgctactggcgttcaggggaaagagg
ccccccctggactcgtgctgcctggggatccaggtcctaagg
gggatcccggcgatagaggcccaatcggcctgaccggcaga
gctggtcccctggcgattccggtcctccggggaaaaagg
ggaccccggtagaccaggtcccccaggccctgttggccctc
gcggaagagatggcgaagtgggagaaaagggcgacgaagga
ccccaggggacccaggacttccaggcaaggctggggagag
aggactgaggggcgctccaggtgtcagaggccctgtcggcg
agaaggggatcagggcgatccaggcgaggacggcagaaac
ggctcccctggctctagtggtccaaaaggcgaccggggaga
gcctgggcctcctgggccaccaggcagactggtcgataccg
gacctggggccagagagaagggcgaaccaggggatagggc
caagaaggcccacgaggaccaaagggcgacccaggattgcc
tggcgctcctggcgagaggggcatcgagggctttagaggtc
cacccggtccccaaggcgaccccggcgttaggggacctgct
ggggagaagggcgacagaggcccacccggactggacggcag
atctggcctggatggcaagcctggcgccgctggcccatctg
gacctaacggcgctgctggcaaagccggggaccctggacga
gatggactgccagggctgcggggagaacagggccttccagg
accttcaggaccacctggcctccctggcaagcccggggagg
atggaaagcccggcctgaatggaaaaaacggggaacccggg
gatcctggggaggacggacgcaagggggaaaagggcgattc
cggcgcctctggcagagagggcagggacggaccaaaagggg
agcgcggagcacccggcattctgggtcctcagggggccacct
ggattgccaggtccagttggtcctcctggccaggggtttcc
cggcgtcccaggcggtacagggcctaaaggggatagaggcg
agacaggcagcaaaggggaacaggggctcccaggcgaaagg
ggcttgagaggcgagcctggctccgtgcctaacgtggacag
actgctggaaaccgccggcatcaaggcctccgccctgcgcg
agatcgtggaaacctgggacgagtcctccggctccttcctg
cccgtgcctgagcgcagaagggcccgaaaggggactctgg
cgagcaaggaccacccggcaaagagggacccatcggcttcc
ctggggagcgggggttgaaaggcgataggggagatccaggc
ccacaagggcctccagggctggcacttggagagcgtggtcc
tccaggaccaagcggactggcaggggagcccggaaagcctg
gaatccccgggttgcctggtagagccggcggagtgggcgaa
gcaggcaggcctggggaacgcggagagagaggcgaaaaggg
cgaaagaggggagcagggccgcgacggtccccccggactac
ctggaactccagggcccccaggacccccggacctaaggtg
tccgtggatgagcctggccccggactgagcggagaacaagg
tccacctggcttgaagggtgccaaggggggagccaggctcta
acggcgatcaagggcccaaggggggatcggggagtgcctggc
atcaaagggggaccggggcgaacccggtcctagagggcaaga
cggaaaccccggcttgccgggcgaacggggaatggctggtc
ccgagggaaagccaggcttgcagggacctaggggggcctccc
ggtcctgtgggtggacatggcgatccgggtccaccaggtgc
tccaggactcgctggtccagcaggccctcagggaccatccg
gcctgaaagggggaaccaggcgaaactggccccccaggcaga
ggcctgacaggccctactggtgctgtgggcctccctggacc
tcctggccctagtggactcgtgggccctcagggctctcccg
gactgccaggccaagtgggcgagactggaaaacccggggct
cccggcagggatggcgcttctggaaaagacggcgataggggg
cagccctggcgtgcccggtagtccagggctacctggccctg
tgggtcccaaaggggagcctggacctacaggcgcaccaggc
caggctgtagtggggctgcctggcgctaaaggcgagaaggg
tgctcctggcggcctggctggcgatctcgttggagaacctg
gcgccaagggcgaccgtggcttgccaggacctcgcggcgag
aaaggcgaagctggcagagctggcgagcctggggacccagg
cgaagatggccagaaaggcgctcccggccctaagggattca
agggcgatccgggcgtgggcgtgccaggctctccaggtcct
cctggaccacccggtgtcaagggcgatttgggccttcctgg
cctgccaggggcacctggcgtcgtgggctttcctggacaga
ccggcccacggggagagatgggacagccaggccccagcgga
gaaagagggctggctggccccgcctggcagggaaggcatacc
aggcccattggggcctccaggcccacctggatctgtggggc
ctcctggcgcctctggactgaaaggcgacaaaggcgatcct
ggtgtcggcctgccaggcccaagaggcgagagggagagcc
cggcatcaggggcgaagatggacggcctggccaagagggcc
ctcggggattgaccggccctcctggatccagaggcgaacgg
ggggagaaggggacgtgggctctgctggcctcaaaggcga
caaggggactccgccgtgattctgggccctccggaccctc
ggggagctaaggggacatgggagagaggggtccacgggga
ctggatgggacaagggaccacgcggagacaacggcgaccc
gggggataagggctccaagggcgaacctggcgataagggat
ccgctggactgcctggcctgaggggcctgctgggacctcaa
ggacaaccaggcgccgcaggcatccctggcgaccctggatc
tcctggaaaggacggcgtgcccggcatccgcggagaaaagg
gggatgtcggcttcatgggccccaggggggctgaaggggaa
aggggagtgaagggcgcttgcggcctcgatgggaaagggg
ggacaagggggaggctggccctccaggacgacctggactgg
```

-continued

```
ctggccacaagggcgaaatgggagagccaggcgtgcccgga
cagtccggcgctccaggcaaagagggcctgatcggcccaa
aggcgatagaggatttgacggccagcctggcccaaagggcg
atcaaggcgaaaaaggggagagaggcaccccggcatcggc
ggctttccaggcccctctggaaacgatggctctgccggccc
acctgggccacctggtagtgtgggaccaagaggccccgagg
gactgcagggacagaaaggcgagagagggcccctggcgag
agagttgtgggagcacctggcgttccggcgcacccggcga
aaggggagaacaaggcagacctggaccagccggaccccgtg
gggaaaaaggcgaggccgcctgaccgaggacagatcaga
ggcttcgtgcggcaagagatgtcccagcactgcgcctgtca
gggccagtttatcgcctccggcagcagaccccctgccttcct
acgctgccgataccgccggctctcagctgcacgctgtgcct
gtgctccgggtgtcccacgccgaggaagaggaaagagtccc
tcctgaggacgacgagtacagcgagtactctgagtattccg
tggaagagtaccaggatcccgaggcccttgggacagcgac
gaccttgctccctgcctctggatgagggctcctgcaccgc
ctacaccctgagatggtatcaccgggccgtgacaggctcca
ccgaggcctgtcacccttttcgtgtatggcggctgcggcggc
aacgccaatagattcggcaccgcgaggcctgcgagcggag
atgtcctcccagagtggtgcagtcccagggcaccggcacag
cccaggactgatagtctagagtggccggcc
```

An amino acid sequence for human collagen 7 is as follows:

(SEQ ID NO: 2)
```
mtlrllvaalcagilaeaprvraqhrervtctrlyaadivf
lldgsssigrsnfrevrsflegvlvlpfsgaasaqgvrfatv
qysddprtefgldalgsggdvirairelsykggntrtgaai
lhvadhvflpqlarpgvpkvcilitdgksqdlvdtaaqrlk
gqgvklfavgiknadpeelkrvasqptsdffffvndfsilr
tllplvsrrvcttaggvpvtrppddstsaprdlvlsepssq
slrvqwtaasgpvtgykvqytpltglgqplpserqevnvpa
getsvrlrglrplteyqvtvialyansigeavsgtartal
egpeltiqnttahsllvawrsvpgatgyrvtwrvlsggptq
qqelgpgqgsvllrdlepgtdyevtvstlfgrsvgpatslm
artdasveqtlrpvilgptsillswnlvpeargyrlewrre
tgleppqkvvlpsdvtryqldglqpgteyrltlytlleghe
vatpatwptgpelpvspvtdlqatelpgqrvrvswspvgga
tqyriivrstqgvertlvlpgsqtafdlddvqaglsytvrv
sarvgpregsasvltvrrepetplavpglrvvvsdatrvrv
awgpvpgasgfriswstgsgpessqtlppdstatditglqp
gttyqvavsvlrgreegpaavivartdplgpvrtvhvtqas
sssvtitwtrvpgatgyrvswhsahgpeksqlvsgeatvae
ldglepdteytvhvrahvagvdgppasvvvrtapepvgrvs
rlqilnassdvlritwvgvtgatayrlawgrseggpmrhqi
lpgntdsaeirgleggvsysvrvtalvgdregtpvsivvtt
ppeappalgtlhvvqrgehslrlrwepvpraqgfllhwqpe
ggqeqsrvlgpelssyhldglepatqyrvrlsvlgpagegp
saevtartesprvpsielrvvdtsidsvtplawtpvsrass
yilswrplrgpgqevpgspqtlpgisssqrvtglegvsyif
sltpvldgvrgpeasvtqtpvcprgladvvflphatqdnah
raeatrrvlerlvlalgplgpqavqvgllsyshrpsplfpl
ngshdlgiilqrirdmpymdpsgnnlgtavvtahrymlapd
apgrrqhvpgvmvllvdeplrgdifspireaqasglnvvml
gmagadpeqlrrlapgmdsvqtffavddgpsldqavsglat
alcqasfttqprpepcpvycpkgqkgepgemlrgqvgppg
dpglpgrtgapgpqgppgsatakgergfpgadgrpgspgra
gnpgtpgapglkgspglpgrgdpgergprgpkgepgapgq
viggegpglpgrkgdpgpsgppgprgplgdpgrgppglpg
tamkgdkgdrgergppgpgeggiapgepglpglpgspgpqg
pvgppgkkgekgdsedgapglpgqpgspgeqgprgppgaig
pkgdrgfpgplgeagekgergppgpagsrglpgvagrpgak
gpegppgptgrqgekgepgrpgdpavvgpavagpkgekgdv
gpagprgatgvqgergppglvlpgdpgpkgdpgdrgpiglt
gragppgdsgppgekgdpgrpgppgpvgprgrdgevgekgd
egppgdpglpgkagerglrgapgvrgpvgekgdqgdpgedg
rngspgssgpkgdrgepgppgppgrlvdtgpgarekgepgd
rgqegprgpkgdpglpgapgergiegfrgppgpqgdpgvrg
pagekgdrgppgldgrsgldgkpgaagpsgpngaagkagdp
grdglpglrgeqglpgsgppglpgkpgedgkpglngknge
pgdpgedgrkgekgdsgasgregrdgpkgergapgilgpqg
ppglpgpvgppgqgfpgvpggtgpkgdrgetgskgeqglpg
erglrgepgsvpnvdrlletagikasalreivetwdessgs
flpvperrgpkgdsgeqgppgkegpigfpgerglkgdrgd
pgpqgppglalgergppgpsglagepgkpgipglpgraggv
geagrpgergergekgergeqgrdgppglpgtpgppgppgp
kvsvdepgpglsgeqgppglkgakgepgsngdqgpkgdrgv
pgikgdrgepgprgqdgnpglpgergmagpegkpglqgprg
ppgpvgghgdpgppgapglagpagpqgpsglkgepgetgpp
grglgptgavglpgppgpsglvgpqgspglpggqvgetgkp
gapgrdgasgkdgdrgspgvpgspglpgpvgpkgepgptga
```

-continued

```
pgqavvglpgakgekgapgglagdlvgepgakgdrglpgpr gekgeagragepgdpgedgqkgapgpkgfkgdpgvgvpgsp gppgppgvkgdlglpglpgapgvvgfpgqtgprgemgqpgp sgerglagppgregipgplgppgppgsvgppgasglkgdkg dpgvglpgprgergepgirgedgrpgqegprgltgppgsrg ergekgdvgsaglkgdkgdsavilgppgprgakgdmgergp rgldgdkgprgdngdpgdkgskgepgdkgsaglpglrgllg pgqgpgaagipgdpgspgkdgvpgirgekgdvgfmgprglk gergvkgacgldgekgdkgeagppgrpglaghkgemgepgv pgqsgapgkegligpkgdrgfdgqpgpkgdqgekgergtpg iggfpgpsgndgsagppgppgsvgprgpeglqgqkgergpp gervvgapgvpgapgergeqgrpgpagprgekgeaaltedd irgfvrqemsqhcacqgqfiasgsrplpsyaadtagsqlha vpvlrvshaeeeervppeddeyseyseysveeyqdpeapwd sddpcslpldegsctaytlrwyhravtgsteachpfvyggc ggnanrfgtreacerrcpprvvqsqgtgtaqd
```

Prolidase

Prolidase is a cytosolic imidodipeptidase, which specifically splits imidodipeptides with C-terminal proline or hydroxyproline residues. The enzyme plays an important role in the recycling of proline from imidodipeptides, mostly derived from degradation products of collagen, for resynthesis of collagen and other proline containing proteins. Specific host cells may require supplementation of prolidase to ensure proper synthesis of the recombinant collagen protein (as referenced in (Miltyk et al. *J Biochem* 144(3): 409-414 (2008)). Host cells described herein, recombinantly manipulated to express collagen 7, may be recombinantly manipulated to also express human prolidase. An exemplary amino acid sequence for human prolidase is as follows:

```
                                              (SEQ ID NO: 4)
maaatgpsfwlgnetlkvplalfalnrqrlcerlrknpavqagsivvl qggeetqryctdtgvlfrqesffhwafgvtepgcygvidvdtgkstlf vprlpashatwmgkihskehfkekyavddvqdeiasvltsqkpsvllt lrgvntdsgsvcreasfdgiskfevnntilhpeivecrvfktdmelev lrytnkisseahrevmkavkvgmkeyeleslfehycysrggmrhssyt cicgsgensavlhgagapndrtiqngmclfdmggeyycfasditcsfp angkftadqkavyeavlrssravmgamkpgvwwpdmhrladrihleel ahmgilsgsvdamvqahlgavfmphglghflgidvhdvggypgvride pglrslrtarhlqpgmvltvepgiyfidhlidealadparasflnrev lqrfrgfggvrieedvvvtdsgielltcvprtveeieacmagcdkaft pfsgpk
```

An exemplary nucleic acid sequence encoding human prolidase is provided below:

```
                                              (SEQ ID NO: 3)
   1 ccggtgccgg gcgaacatgg cggcggccac cggaccctcg ttttggctgg ggaatgaaac 61 cctgaaggtg ccgctggcgc tctttgcctt gaaccggcag cgcctgtgtg agcggctgcg 121 gaagaaccct gctgtgcagg ccggctccat cgtggtcctg cagggcgggg aggagactca 181 gcgctactgc accgacaccg ggtcctctt cctccaggag tccttctttc actgggcgtt 241 cggtgtcact gagccaggct gctatggtgt catcgatgtt gacactggga agtcgaccct 301 gtttgtgccc aggcttcctg ccagccatgc cacctggatg gaaagatcc attccaagga 361 gcacttcaag gagaagtatg ccgtggacga cgtccagtac gtagatgaga ttgccagcgt 421 cctgacgtca cagaagccct ctgtcctcct cactttgcgt ggcgtcaaca cggacagcgg 481 cagtgtctgc agggaggcct cctttgacgg catcagcaag ttcgaagtca acaataccat 541 tcttcaccca gagatcgttg agagccgagt gtttaagacg gatatggagc tggaggttct 601 gcgctatacc aataaaatct ccagcgaggc ccaccgtgag gtaatgaagg ctgtaaaagt 661 gggaatgaaa gaatatgggt tggaaagcct cttcgagcac tactgctact ccggggcgg 721 catcgccac agctcctaca cctgcatctg cggcagtggt gagaactcag ccgtgctaca 781 ctacggacac gccggagctc ccaacgaccg aacgatccag aatggggata tgtgcctgtt 841 cgacatgggc ggtgagtatt actctgtcgc ttccgacatc acctgctcct tccccgcaa 901 cggcaagttc actgcagacc agaaggccgt ctatgaggca gtgctgctga gctcccgtgc 961 cgtcatgggt gccatgaagc aggtgactg gtggcctgac atcgaccgc tggctgaccg 1021 catccacctg gaggagctgg cccacatggg catcctgagc ggcagcgtgg acgccatggt 1081 ccaggctcac ctgggggccg tgtttatgcc tcacgggctt ggccacttcc tgggcattga 1141 cgtgcacgac gtgggaggct acccagaggg cgtggagcgc atcgacgagc ccggcctgcg
```

-continued

```
1201  gagcctgcgc actgcacggc acctgcagcc aggcatggtg ctcaccgtgg agccgggcat 1261  ctacttcatc gaccacctcc tggatgaggc cctggcggac ccggcccgcg cctccttcct 1321  taaccgcgag gtcctgcagc gctttcgcgg ttttggcggg gtccgcatcg aggaggacgt 1381  cgtggtgatc gacagcggca tagagctgct gacctgcgtg ccccgcactg tggaagagat 1441  tgaagcatgc atggcaggct gtgacaaggc ctttaccccc ttctctggcc ccaagtagag 1501  ccagccagaa atcccagcgc acctgggggc ctggccttgc aacctctttt cgtgatgggc 1561  agcctgctgg tcagcactcc agtagcgaga gacggcaccc agaatcagat cccagcttcg 1621  gcatttgatc agaccaaaca gtgctgtttc ccggggagga aacacttttt taattaccct 1681  tttgcaggca ccacctttaa tctgttttat accttgctta ttaaatgagc gacttaaaat 1741  gattgaaaat aatgctgtcc tttagtagca agtaaaatgt gtcttgctgt catttatatt 1801  ccttttccca ggaaagaagc atttctgata ctttctgtca aaaatcaata tgcagaatgg 1861  catttgcaat aaaaggtttc ctaaaatg
```

Glycosyl Transferase

Mammalian host cells, such as CHO cells, may be employed to produce glycosylated recombinant proteins, such as collagen 7, because they are equipped with glycosylation machinery similar to the human. However, a notable difference concerns sialylation: N-linked glycans of human origin carry terminal sialic acid residues in both K2,3- and K2,6-linkages, whereas only K2,3 terminal sialic acids are found in glycoproteins from CHO and BHK cells. Indeed, these cell lines lack a functional copy of the gene encoding K2,6-sialyltransferase (Bragonzi et al. Biochim Biophys Acta 1474(3): 273-82 (2000)). Host cells may be recombinantly manipulated to express the human glycosyl aminotransferase, rST6Ga11, before, after, or simultaneously with manipulating said host cell to recombinantly express collagen 7 or collagen 7 and prolidase.

Amino acid sequence for *rattus norvegicus* ST6 beta-galactosamide alpha-2,6-sialyltransferase 1 (St6gall), transcript variant 1 (rST6Ga11)

```
                                                  (SEQ ID NO: 5)
mihtnlkkkfslfilvfllfavicvwkkgsdyealtlqakefqmpksq ekvamgsasqvvfsnskqdpkedipilsyhrvtakvkpqpsfqvwdkd stysklnprllkiwrnylnmnkykvsykgpgvkfsvealrchlrdhvn vsmieatdfpfntteweqylpkenfrtkvgpwqrcavvssaqslknsq lgreidnhdavlrfngaptdnfqqdvgskttirlmnsqlvttekrflk dslytegilivwdsyhadipkwyqkpdynffetyksyrrlnpsqpfyi lkpqmpwelwdiiqeisadliqpnppssgmlgiiimmticdqvdiyef lpskrktdvcyyhqkffdsactmgayhplifeknmvkhlnegtedylf gkatlsgfrnirc
```

Nucleotide sequence for human ST6 beta-galactosamide alpha-2,6-sialyltransferase 1 (St6gall), transcript variant 1 (rST6Ga11) can be optimized.

Prolyl Hydroxylase

An exemplary prolyl hydroxylase is described below:

```
                                                  (SEQ ID N: 6)
  1  mahhhhhhlp alklaleyiv pcmnkhgicv vddflgketg qqigdevral hdtgkftdgq 61  lvsqksdssk dirgdkitwi egkepgceti gllmssmddl irhcngklgs ykingrtkam 121  vacypgngtg yvrhvdnpng dgrcvtciyy lnkdwdakvs ggilrifpeg kaqfadiepk 181  fdrllffwsd rrnphevqpa yatryaitvw yfdaderara kvkyltgekg vrvelnkpsd 241  svgkdvf
```

Heat Shock Protein 47 (HSP47)

HSP47 is a chaperone protein resident in the endoplasmic reticulum which functions in procollagen formation. HSP47 assists in the translocation of procollagen into the endoplasmic reticulum. HSP47 also helps maintain the emerging polypeptide in an unfolded state until synthesis is complete, and release of procollagen from HSP47 is driven by procollagen helical formation. Host cells of the present invention may be recombinantly manipulated to express the human HSP47, before, after, or simultaneously with manipulating said host cell to recombinantly express collagen 7 or collagen 7 and prolidase.

Cyclophilin B (Cyp B)

Cyclophilin B is a peptidyl-prolyl cis-trans isomerase found in the endoplasmic reticulum. B functions in consort with HSP47 to facilitate the folding and transport of procollagen. Host cells of the present invention may be recombinantly manipulated to express the human cyclophilin B, before, after, or simultaneously with manipulating said host cell to recombinantly express collagen 7 or collagen 7 and prolidase.

Protein disulfide isomerase (PDI)

Protein Disulfide Isomerase (PDI) is an ER resident thiol oxidoreductase protein. PDI assists in protein folding in part through catalyzing of the formation, reduction, and isomerization of disulphide bonds. PDI facilitates the stabilization of collagen trimers through catalyzing the formation of interchain disulphide bonds between the C-propeptide domains. Host cells of the current invention may be recombinantly manipulated to express the human PDI, before, after, or simultaneously with manipulating said host cell to recombinantly express collagen 7 or collagen 7 and prolidase.

Oxoglutarate Carrier (OGC)

Oxoglutarate carrier (OGC) is a mitochondrial resident protein which transports the α-ketoglutarate across the inner membrane of the mitochondria and facilitates the coupling of decarboxylated α-ketoglutarate to proline. Host cells may be recombinantly manipulated to express the human OGC, before, after, or simultaneously with manipulating said host cell to recombinantly express collagen 7 or collagen 7 and prolidase.

Vectors

Suitable vectors for use herein are those that can express collagen 7, prolidase, glycosyl-transferase, HSP47, cyclophilin B, PDI, OGC, or a molecular chaperone involved in procollagen assembly or folding, or a functional portion thereof. In order to express the proteins described herein, the nucleotide sequence encoding the appropriate protein, or a functional equivalent, can be inserted into a suitable vector. A suitable vector contains the necessary and appropriate transcriptional and translational control sequences for expression of the inserted nucleic acid sequence. Standard methods, known to those skilled in the art, may be used to construct the recombinant expression vectors containing the nucleic acid sequences described herein. These methods include, but not limited to, in vitro recombinant techniques, synthetic techniques, and in vivo recombination/genetic recombination; the choice of method depends on the nature of the specific nucleotide fragments and may be determined by persons skilled in the art.

Suitable vectors for use herein may contain an origin of replication and a restriction endonuclease sequence site. Persons skilled in the art would have knowledge of suitable origin of replication and restriction endonuclease sequences for use in the host cell. Suitable vectors for use herein may contain sequence elements to aid transcription, including, but not limited to, promoter and enhancer elements. Persons skilled in the art would have knowledge of various transcriptional control elements, including, but not limited to, promoters, inducible promoters, and enhancer elements, that would be suitable in the host cell. Suitable vectors for use herein may also contain a selectable marker gene that encodes a product necessary for the host cell to grow and survive under specific conditions, aiding in the selection of host cells into which the vector has been introduced. Typical selection genes may include, but not limited to, genes encoding a protein that confers resistance to an antibiotic, drug, or toxin (e.g. tetracycline, ampicilin, neomycin, hygromycin, etc). Persons skilled in the art would have knowledge of coding sequences for suitable selectable markers and reporter genes for use in the host cell.

Expression vectors described herein can be introduced into host cells via conventional transformation or transfection techniques. Transformation and transfection techniques include, but not limited to, calcium phosphate or calcium chloride coprecipitation, DEAE-dextran-mediated transfection, lipofectamine, electroporation, microinjection, and viral mediated transfection (as referenced in U.S. Pat. No. 6,632,637 (McGrew)). Persons skilled in the art would have knowledge of suitable transformation and transfection methods based on the host cell/vector combination. For long term, high yield production of recombinant proteins, stable expression of the recombinant protein may be preferred. Host cells that stably express the recombinant protein may be engineered.

Cells

The recombinant expression vectors described herein may be introduced into a suitable host cell, which may include a living cell capable of expressing the protein coding region from the defined recombinant expression vector. The term "host cell" refers not only to the particular subject cell but to the progeny or potential progeny of the particular subject cell. Because certain modifications may occur in succeeding generations due to either mutation or environmental influences, such progeny may not in fact, be identical to the parent cell, but are still included within the scope of the term as used herein. Various host cell expression systems may be utilized to express the nucleic acid molecules described herein. These include, but are not limited to yeast or fungi, transformed with recombinant yeast or fungi expression vectors containing the appropriate nucleic acid sequence; insect cell systems infected with recombinant virus expression vectors or transformed with recombinant plasmid expression vectors containing the appropriate nucleic acid sequence; or mammalian cell systems (e.g. primate cell, human cell, rodent cell, etc) transfected with expression vectors containing the appropriate nucleic acid sequence. Suitable host cells may include primary or transformed cell lines, including, but not limited to, fibroblasts, CHO, HEK293, C127, VERO, BHK, HeLa, COS, MDCK, etc (as referenced in U.S. Pat. No. 6,632,637 (McGrew)). Other suitable host cells are known to those skilled in the art.

Modifications, including, but not limited to, glycosylation, phosphyorylation and processing of protein products may be important to the function of a protein. Different host cells have various characteristics and mechanisms for post-translational processing and modification of proteins. A host cell that is capable of modulating expression of the nucleic acid sequences contained in the vector, or modulating expression of the vector nucleic acid sequences, or modifying and processing the gene product encoded in the vector sequence in a specific manner may be chosen. Mammalian host cells may be chosen to ensure the correct modification and processing of the recombinant protein. Such mammalian host cells may include, but not limited to, CHO, HEK293, human fibroblasts, and human keratinocytes.

Cell Culture

Standard cell culture procedures and conditions may be used for culture of host cells described herein and are known to those skilled in the art. Host cells cultured for expression of recombinant collagen 7, such as HEK293 cells, may be cultured in routinely used cell culture media (e.g. Dulbecco's modified Eagle's medium (DMEM)/Ham's F-12 (1:1) with suitable supplementation of serum, antibiotics, etc, dependent on the application) as referenced in, ((Chen et al. *J Bio Chem* 277(18): 2118-2124 (2002)), (Chen et al. *J Bio Chem* 275: 32(11): 24429-24435 (2000)), (Chen et al. *J Bio Chem* 276(24): 21649-21655 (2001)).

Host cells may be engineered to express other proteins to optimize production of the recombinant collagen 7, or a functional fragment thereof. This may include, but not limited to, the coexpression of the processing enzymes prolidase and/or glycosyl-transferase described herein, by exogenously introducing isolated nucleic acid or recombinant expression vectors encoding the appropriate nucleic acid sequence, in host cells comprising collagen 7 nucleic acid sequence or recombinant expression vector. The triple helical assembly of collagen 7 often requires hydroxylation and the presence of ascorbic acid in the host cell growth media. As demonstrated in the reference, (Chen et al. *J Bio Chem* 277 (18): 2118-2124 (2002)), recombinant type 7 collagen produced, recovered, and purified from HEK293 cells in the presence of ascorbic acid was secreted as an approximately 900-kDa protein, corresponding to the association of three type 7 collagen monomers (each monomer 290-kDa). Ascorbic acid may be used in the host cell culture conditions to aid in proper processing of the recombinant protein. Additional supplements to the cell culture media may be added in order to aid in proper processing of the recombinant protein, including but not limited to, phospho-ascorbate (PAA), 4 mM α-ketoglutarate, $FeSO_4$, or Optiferrin.

Homologous Sequences

The methods and compositions of the present invention encompass polypeptides and nucleic acids having the sequences specified, or sequences substantially identical or similar thereto, e.g., sequences at least 70%, 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%. 91%, 92%, 93%, 94%, 95%, 96%, 97%, 98% or 99% identity to SEQ ID NO:2, SEQ ID NO:4 or SEQ ID NO:6 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 70%, 85%, 90%, 91%, 92%, 93%, 94%, 95%, 96%, 97%, 98% or 99% identity to SEQ ID NO:1, 3, or 5 are termed substantially identical.

The term "functional variant" refers polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to BMP-10/BMP-10 receptor nucleic acid (SEQ ID NO:1) molecules of the invention. BLAST protein searches can be performed with the XBLAST program, score=50, wordlength=3 to obtain amino acid sequences homologous to BMP-10/BMP-10 receptor (SEQ ID NO:1) protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov.

Also included herein are sequences that hybridize under low, medium or high stringency to a recited nucleic acid. As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Purification of Collagen 7, or a Functional Fragment Thereof

Proteins produced by recombinant methods described herein may be recovered from the host cell culture system according to standard protocols known in the art (e.g., precipitation, centrifugation, etc). Recombinant collagen 7 described herein may be secreted into the host cell medium and recovered by ammonium sulfate precipitation and subsequent centrifugation; as demonstrated in the following reference, (Chen et al. *J Bio Chem* 277(18): 2118-2124 (2002)). Proteins produced and recovered by recombinant and molecular biology methods described herein, may be purified according to standard protocols known in the art (e.g., dialysis, ion exchange chromatography, affinity chromatography, SDS gel electrophoresis, etc). The recombinant collagen 7 described herein may be purified to homogeneity by ion exchange chromatography; as demonstrated in the following reference, (Chen et al. *J Bio Chem* 277(18): 2118-2124 (2002)).

EXEMPLIFICATION

Example 1

Production and Purification of Collagen 7

Subculturing and Freezing the Cells
1. Wash the cells with PBS (10 ml for P150 plate).
2. Add 6 ml of trypsin (0.05% trypsin-EDTA in PBS) and incubate at 37° C. incubator for 4 to 6 minutes. Cells will detach as a layer.
3. Add 6 ml of growth medium and then spin down at conical centrifuge at 2K for 5 minutes.
4. Resuspend the cells in growth medium and subculture cells at 1:5 ratio.
5. For freezing the cells, we use growth medium with 10% DMSO. A confluent P150 plates will give rise to approximately 20 millions of cells.

Defrost and Re-Growth the Cells
1. Take a viral of RDEB/FB/C7 ($5 \times 10^6$) and thaw in 37° C. water bath briefly.
2. Put into a P150 plate containing 20 ml of growth medium and incubate overnight.
3. Change to the fresh medium at second day. Cells should reach confluent after 2 to 3 days.
4. Take out 30 μl medium directly and subject to immunoblot with anti-type VII collagen antibody to insure the presence of type VII collagen in the medium.

Growth and Harvest Medium

Growth medium: DMEM/F12 (1:1) with L-glutamine and L sodium bicarbonate (Mediatech, Inc., DMEM prepares 10 L at 13.48 g/L Cat. No. 50-003-PB and Ham's F-12 Medium prepares 10 L at 10.64 g/L Cat. No. 50-040-PB), 10% FBS (Omega Scientific Cat# FB-02) and 200 μg/ml ascorbic acid (Sigma CAT# A4544) (1 ml stock solution of 100 mg/ml added to 500 ml medium).

Serum free medium: DMEM/F12 without serum and ascorbic acid.

1. Grow gene-corrected RDEB fibroblasts in P150 plates in 20 ml of growth medium till confluence.
2. Add 15 ml of serum free medium in the morning (for example Monday morning).
3. Harvest medium in the next afternoon and add back 20 ml of growth medium to the cells (Tuesday afternoon).
4. Two days later, add serum free medium in the morning again (Thursday morning).
5. Harvest the medium again next afternoon (Friday afternoon).
6. Repeat this cycle on following Monday for at least 3 to 4 months till cells detach (some time cells can go on for 6 months and still secrete a lot of type VII collagen).

The serum free media of gene corrected fibroblasts contain approximately 4 to 8 mg/L type VII collagen. After purification, between 0.7 to 1 mg of type VII collagen in normally obtained from 1 liter media.

Purification of Type VII Collagen

| Materials: | Ammonium Sulfate |
| --- | --- |
| | EDTA: 500 mM, pH 8 |
| | NEM: 100 mM |
| | PMSF: 100 mM |
| | Q Sepharose ™ Fast Flow |
| | (GE Healthcare CAT# 17-0510-01) |
| 1X Buffer A: | 65 mM NaCl |
| | 25 mM Tris-HCl pH 8.6 |
| | 1 mM EDTA |

| For 2 L 10X buffer A: | 76.11 g NaCl |
| --- | --- |
| | 250 ml 2M Tris-HCl pH 8.6 |
| | 40 ml 0.5M EDTA |
| Buffer B: | 50 mM Tris pH 7.8 |
| | 150 mM NaCl |
| | 5 mM EDTA |
| | 2 mM MEM |
| | 2 mM PMSF |
| Buffer C: | 50 mM Tris pH 7.5 |
| | 2M Urea |
| | 0.5M NaCl |
| | 1 mM EDTA |
| | 2 mM MEM |
| | 2 mM PMSF |

DAY 1
1. Collect conditioned cell medium and spin at 3000 rpm for 10 min in 4° C. to remove the cell debris.
2. Measure the harvest volume (Total Media collected)
3. Add inhibitors: 5 mM EDTA (100 fold), 50 µM NEM and 50 µM PMSF (2000 fold)
4. Slowly add Ammonium Sulfate powder on ice: 0.3 g/mL
5. Stir overnight at 4° C.
DAY 2
6. Spin at 13,000 rpm in Beckman J2-M1 rotor 14 for 1.5-2 hours
7. Discard supernatant, then air-dry pellet for 10-15 min.
8. Bring pellet up in Buffer A: Use 1 ml of buffer per 50 ml of the harvest volume.
9. Rinse the dialysis membrane with DI $H_2O$
10. Dialyze against 1× Buffer A for 3 times: change every 2 hours, 2 Liter for each change. Last change is for overnight. Add 1 ml NEM and PMSF to dialysis buffer.
DAY 3
11. Spin down dialyzed media at 9K for 20 min. Note change in volume.
12. Remove supernatant (S1) and put in a separate tube.
13. Resuspend pellet in an equal volume of Buffer B as dialysis volume.
14. Let this sit out on top of bench for about 10 minutes.
15. Centrifuge at 9K for 20 min
16. Remove supernatant (S1') and place in another tube.
17. Resuspend the pellet in 2 ml of Buffer C centrifuge at 9 k for 20 min and collect supernatant (S2). Type VII collagen will be present in all fractions with different purity. S1 fraction contains approximately 50% type VII collagen but is very dirty. Typically the S1 fraction is not used for further purification. With good dialysis, most will be in S1' in a purer form. With sub-optimal dialysis, most will be in the S1 fraction, and very dirty. Typically, the S1' fraction is subject to further Q-sepharose column purification.

Type VII Collagen Column Purification from S1'.
18. Fill column with sepharose beads ((beads must be shaken into solution before use) and let settle to desired volume.

The column volume should be approx. ½ loading volume of sample from S1'.
19. The column should not be allowed to dry out. Wash with buffer B 5× column volume (therefore if 4 ml column then wash with 20 ml buffer B)
20. Prepare wash and elution tubes with equal volume as column volume.
21. Save 200 µl of protein sample in small eppendorf and store on ice (to run on gel at end for control)
22. Make and label tubes: 2× wash (buffer B), 0.3M, 0.4M, and 1.0M.
Everything with a 2× in front of it means 2 times column volume (therefore if column volume is 4 ml then use 8 ml) Load sample to column, being careful not to excessively disturb the column surface. Place tube labeled "flow through" to collect the flow through.
23. Keep everything on ice. When the sample has flowed through once, load the flow through again and collect flow through with tube labeled "flow through."
24. Before the column runs dry, wash with buffer B (equivalent to sample volume) TWICE and collect with tube labeled wash (therefore if 4 ml then 8 ml buffer B). Continue eluting with increasing salt concentration and ending with 1.0M. 2× wash (buffer B), 2× 0.3M, 2× 0.4M and 1.0M A, 1.0M B. (Note: most C7 comes out at 1.0 M). Everything with a 2× in front of it means 2 times column volume (therefore if column volume is 4 ml then use 8 ml)
25. Add inhibitors PMSF and NEM. 1:100 fold dilutions to each elution tube (therefore if 40 ml use 40 µl). Most C7 will come out in 0.5-1M eluted fractions.
26. Make samples to run on gel (gel only holds 9 samples at a time). Label 9 small eppendorf tubes× 2 (one for western blot and the other for Coomassie staining): load on, follow through, 0.3M, 0.4M . . . 1.0M
27. Make loading dye: 12 µl BME/100 µl of 4× sample buffer vortex.
28. Add 10 µl of the dye to all tubes.
29. Add 10 µl of sample for ECL, 40 µl for Coomassie Blue to tubes.
30. Run collected fractions on a 6% acrylamide gels for both Western blot analysis and Coomassie Blue staining.

Concentration and Filtration of Type VII Collagen
1. Combined type VII collagen fractions from 0.5, 0.7 and 1.0 M elution and dilute with buffer B three fold (for example, 17 ml to 50 ml).
2. Load 50 ml of diluted fraction into a 1.5 ml Q-sepharose column two times.
3. Wash column two times with 1.5 ml buffer B.
4. Elute column with buffer B in 1.0 M salt three times (labeling tube as 1.0A, 1.0B and 1.0C).
5. Dialyze the concentrate with PBS.
6. Filter with 0.2 µm Super Membrane Acrodisc Syringe Filter (Pall Life Sciences).
7. Store at −80° C. Freezer.

Other embodiments are within the following claims.

What is claimed is:

1. A method of making human collagen 7, or a functional fragment of human collagen 7, comprising:
 providing a cell, which comprises an exogenously introduced nucleic acid that encodes human collagen 7, or a functional fragment thereof, wherein said cell is recombinantly manipulated to express one or more polypeptides that increase expression of human collagen 7, or a functional fragment thereof, and wherein the one or more polypeptides comprises prolidase; and
 culturing said cell under conditions sufficient for the production of human collagen 7, or the functional fragment of human collagen 7, and prolidase, thereby making human collagen 7, or the functional fragment thereof.

2. The method of claim 1, wherein said cell is genetically manipulated to express a glycosyl transferase.

3. The method of claim 1, wherein said cell comprises an exogenously introduced nucleic acid that encodes prolidase.

4. The method of claim 2, wherein said cell comprises an exogenously introduced nucleic acid that encodes the glycosyl transferase.

5. The method of claim 1, wherein said cell comprises an expression vector that comprises a sequence that encodes human collagen 7.

6. The method of claim 1, further comprising recovering human collagen 7, or functional fragment thereof, from said cultured cell.

7. The method of claim 1, wherein at least 30, 40, 50, 60, 70, 80, 90 or 95% of said human collagen 7, or functional fragment thereof, is incorporated into homotrimers.

8. The method of claim 1, wherein at least 30, 40, 50, 60, 70, 80, 90 or 95% of said human collagen 7, or functional fragment thereof, is incorporated into hexamers.

9. The method of claim 1, wherein the exogenously introduced nucleic acid that encodes human collagen 7, or the functional fragment thereof, is a high glycine codon-optimized nucleic acid sequence.

10. The method of claim 1, wherein the cell is a fibroblast.

11. A cell comprising:
 a first expression vector comprising a first nucleic acid sequence that encodes human collagen 7 or a functional fragment thereof,
 a second expression vector comprising a second nucleic acid sequence that encodes one or more polypeptides that increase expression of human collagen 7, wherein said one or more polypeptides comprises prolidase, and
 optionally a third expression vector comprising a third nucleic acid sequence that encodes glycosyl transferase.

12. The cell of claim 11, which is in a cell culture.

13. A cell comprising:
 a vector comprising a first nucleic acid sequence that encodes human collagen 7 or a functional fragment thereof, a second nucleic acid sequence that encodes prolidase, and optionally a third nucleic acid sequence that encodes glycosyl transferase.

14. A method of making a cell suitable for expressing human collagen 7, or a functional fragment thereof, comprising
 recombinantly manipulating said cell to express recombinant human collagen 7, or the functional fragment thereof; and
 recombinantly manipulating said cell to express one or more polypeptides that increase expression of human collagen 7, wherein the one or more polypeptides comprises recombinant prolidase;
 thereby making a cell suitable for expressing recombinant human collagen 7, or the functional fragment thereof.

15. The method of claim 14, further comprising recombinantly manipulating said cell to express recombinant glycosyl transferase.

* * * * *

UNITED STATES PATENT AND TRADEMARK OFFICE
CERTIFICATE OF CORRECTION

PATENT NO. : 9,676,837 B2
APPLICATION NO. : 14/236403
DATED : June 13, 2017
INVENTOR(S) : Malini Viswanathan and Mark de Souza It is certified that error appears in the above-identified patent and that said Letters Patent is hereby corrected as shown below:

On the Title Page

At item (75), delete:
"Inventors: Malini Viswanathan, Action, MA (US);
Mark DeSouza, Boston, MA (US)"

And insert:
--Inventors: Malini Viswanathan, Acton, MA (US)
Mark de Souza, Boston, MA (US)--

Signed and Sealed this
Fifth Day of December, 2017

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 6

<210> SEQ ID NO 1
<211> LENGTH: 8886
<212> TYPE: DNA
<213> ORGANISM: Homo sapiens

<400> SEQUENCE: 1

```
aagcttcgaa gtttaaactg agtgccgcca ccatgaccct gcggctgctg gtggctgccc      60
tgtgtgctgg catcctggcc gaggctccta gagtgcgggc ccagcaccgc gagagagtga     120
cctgcaccag actgtacgcc gccgatatcg tgttcctgct ggacggctcc tcctccatcg     180
gccggtccaa cttccgggaa gtgcggtcct tcctggaagg cctggtgctg ccttctccg      240
gcgctgcctc tgcccagggc gtcagattcg ccaccgtgca gtactccgac gaccccgga      300
ccgagttcgg cctggatgct ctgggctctg gcggcgacgt gatccgggcc atcagagagc     360
tgtcctacaa gggcggcaac acccggacag cgccgctat cctgcacgtg gccgaccatg      420
tgtttctgcc ccagctggcc agacccgcg tgcccaaagt gtgcatcctg atcaccgacg      480
gcaagtccca ggacctggtg acaccgccg ctcagagact gaagggccag ggcgtgaagc      540
tgttcgccgt gggcatcaag aacgccgacc ccgaggaact gaagcgggtg gcctcccagc     600
ctacctccga tttcttcttc ttcgtgaacg acttctccat cctgcggacc ctgctgcccc     660
tggtgtctcg gagagtgtgt accaccgctg cggcgtgcc agtgaccgg cctcctgacg       720
attctacctc cgcccctcgg gatctggtgc tgtccgagcc ttccagccag tccctgagag     780
tgcagtggac cgccgcctct ggccccgtga ccggctacaa ggtgcagtac accctctga     840
ccggcctggg ccagcctctg ccttctgagc ggcaagaagt gaacgtccca gccggcgaga     900
catccgtgcg gctgagaggc ctgaggcccc tgaccgagta ccaagtgacc gtgatcgccc     960
tgtacgccaa cagcatcggc gaggccgtgt ccggcaccgc cagaaccaca gccctggaag    1020
gacccgagct gaccatccag aacaccaccg cccactccct gctggtcgct tggagatctg    1080
tgcctggcgc caccggctat cgcgtgacct ggcgagttct gtctggcggc cctacccagc    1140
agcaagagct gggccctgga cagggctctg tgctgctgag ggacctggaa cccggcaccg    1200
actacgaagt gacagtgtcc accctgttcg gcagatccgt gggccctgcc acctctctga    1260
tggccagaac cgacgcctcc gtggaacaga ccctgaggcc tgtgatcctg gccccacca     1320
gcatcctgct gagctggaac ctggtgcccg aggccagagg ctaccggctg aatggcgga     1380
gagagacagg cctggaacct ccccagaagg tggtcctgcc ctccgacgtg accagatacc    1440
agctggatgg cctgcagcct ggcaccgagt acagactgac cctgtacacc ctgctcgagg    1500
gccacgaggt ggccaccccct gctacagtgg tgcctaccgg ccctgagctg cccgtgtccc    1560
ctgtgaccga tctgcaggcc accgagctgc tggccagcg cgtcagagtg tcttggtccc     1620
cagtgccagg cgctacccag taccggatca tcgtgcggtc cacacagggc gtggaaagaa    1680
ccctggtgct ccccggctcc cagaccgcct tcgacctgga tgatgtgcag gccggcctga    1740
gctacaccgt gcgggtgtcc gctagagtgg ccctagaga aggctccgcc agcgtgctga    1800
ccgtgcgcag agagcctgaa acccctctgg ccgtgcccgg actgcggtg gtggtgtctg     1860
atgccaccag agtcagagtg gcctggggcc ctgtgccagg ggcctccggc ttcagaatct    1920
cctggtccac cggctctggc cctgagtcct tcagaccct gccccctgac tccaccgcca    1980
ccgatatcac cggactgcag cccggaacca cctaccaggt ggccgtgtct gtgctgaggg    2040
gcagagaaga gggcccagcc gccgtgatcg tggccaggac agatcctctg ggcccagtgc    2100
ggaccgtgca cgtgacccag gccagctcca gtccgtgac catcacctgg accagagtcc    2160
ctggcgctac aggctacaga gtgtcctggc actctgccca cggccccgag aagtcccagc    2220
tggtgtctgg cgaggccacc gtggctgaac tggacgcct cgagcccgac acagagtaca    2280
cagtgcacgt gcgcgcccat gtggctggcg tggacggacc tcctgcttcc gtggtcgtgc    2340
```

```
gcaccgctcc tgagcccgtg ggaagagtgt cccggctgca gatcctgaac gcctccagcg    2400
acgtgctgcg gatcacctgg gtcggagtga ccggcgctac cgcttacaga ctggcttggg    2460
gcagatctga gggcggaccc atgcggcatc agatcctgcc tggcaacacc gactccgccg    2520
agatcagagg actggaaggc ggcgtgtcct actctgtgcg cgtgaccgcc ctcgtgggcg    2580
acagagaagg caccccgtg tccatcgtgg tcaccacccc tccagaggcc cctccagctc     2640 tgggcacct gcatgtggtg cagcggggcg agcactccct gagactgaga tgggagcctg     2700
tgcctcgggc ccagggcttc ctgctgcatt ggcagcctga aggcggccaa gagcagtcta    2760
gggtgctggg ccccgagctg tccagctacc acctggacgg actggaacca gccacccagt    2820
acagagtgcg gctgtccgtg ctgggacctg ccggcgaggg accttctgcc gaagtgaccg    2880
ccaggaccga gtccctcgg gtgcctcca tcgagctgag agtggtggat accagcatcg      2940
acagcgtgac cctggcctgg accctgtgt cccgggcctc ttcctacatc ctgtcttgga     3000
ggcctctgag gggcccaggc caagaggtgc aggctccc tcagacactg ccaggcatca      3060
gctcctccca gcgcgtgaca ggactcgagc ctggggtgtc ctacatcttc tccctgaccc    3120
ccgtcctgga cggcgtgcgc ggacctgagg cttctgtgac ccagacccca gtgtgcccca   3180
gaggcctggc cgacgtggtc tttctgcctc acgccaccca ggacaacgcc cacagagccg    3240
aggctaccag acgggtgctc gagagactgg tgctggccct gggaccactg ggcccacagg    3300
ctgtgcaagt gggcctgctg tcttactccc accggccctc cccctgttc ccctgaacg      3360 gctctcacga cctgggcatc atcctgcagc ggatccggga catgccctac atggacccct    3420
ccggcaacaa cctgggcacc gccgtggtca gcccaccg gtacatgctg ccccccgatg      3480
ctcctggcag acggcagcat gtccccggcg tgatggtgct gctcgtggac gagcccctgc    3540
ggggcgacat cttcagccct atcagagagg cccaggctag cggcctgaac gtggtcatgc    3600
tgggcatggc tggcgccgac cctgagcagc tgagaaggct ggcccctggc atggactccg    3660
tgcagacctt ctttgccgtg gacgacggcc ccagcctgga tcaggctgtg tctgcctgg    3720 ctaccgccct gtgtcaggcc tccttcacca cccagcccag acccgagcct tgccccgtgt    3780
actgccctaa gggccagaag ggcgagcccg gcgagatggg cctgagagga caagtgggac    3840
ctccaggcga tcccggcctg cctggaagaa caggcgctcc tggacctcag ggccctcctg    3900
gctctgctac cgctaagggc gagagaggct cccaggcgc cgacggcaga cctggctctc    3960
caggcagagc cggcaatcct ggaacacctg gcgccccagg cctgaaggga tctcctggct    4020
tgcctggccc taggggcgac cctggcgaaa gaggacctag aggccctaaa ggcgagccag    4080
gcgcccctgg ccaagtgatc ggcggagaag gacctggact gccggcaga aagggcgatc     4140 ctggcccttc tggcccaccc ggcccaagag gtcctctggg agatcctgga ccaaggggcc    4200
caccaggcct gcccggaaca gctatgaagg gcgataaggg cgacaggggc gagcggggac    4260
caccaggacc aggcgaaggt ggaatcgctc ccggcgaacc tggctgcca ggactgcctg      4320 gatctcccgg accacaggga cctgtgggcc cacctgcaa aaggggag aaaggcgact        4380 ccgaggacgg ggctccagga ttgcccggcc aaccaggctc tcctggcgaa cagggtccca    4440
gaggacctcc ccgcgctatc ggcccaaagg gggacagagg attccctggc ccactgggcg    4500
aggctggcga aaaggcgaa cgcggaccc ctggccctgc cggcagtaga ggacttcctg      4560
gcgttgccgg cagaccaggc gccaagggac ctgaaggccc tcaggccct accggaaggc     4620 agggcgaaaa gggggaacct ggcaggcag gcgacccagc tgttgtggga ccagccgtgg     4680
ctggacccaa aggcgagaaa ggggatgtgg acccgctgg gcctagaggc gctactggcg     4740
```

```
ttcagggga aagaggcccc cctggactcg tgctgcctgg ggatccaggt cctaagggg      4800
atcccggcga tagaggccca atcggcctga ccggcagagc tggtcccct ggcgattccg      4860
gtcctcccgg ggaaaaaggg accccggta gaccaggtcc cccaggccct gttggccctc      4920
gcggaagaga tggcgaagtg ggagaaaagg gcgacgaagg accccagggg acccaggac      4980
ttccaggcaa ggctggggag agaggactga ggggcgctcc aggtgtcaga ggccctgtcg      5040
gcgagaaggg ggatcagggc gatccaggcg aggacggcag aaacggctcc cctggctcta      5100
gtggtccaaa aggcgaccgg ggagagcctg ggcctcctgg gccaccaggc agactggtcg      5160
ataccggacc tggggccaga gagaagggcg aaccagggga tagggggccaa gaaggcccac      5220
gaggaccaaa gggcgaccca ggattgcctg gcgctcctgg cgagagggc atcgagggct      5280
ttagaggtcc acccggtccc caaggcgacc ccggcgttag ggacctgct ggggagaagg      5340
gcgacagagg cccacccgga ctggacggca gatctggcct ggatggcaag cctggcgccg      5400
ctggcccatc tggacctaac ggcgctgctg gcaaagccgg ggaccctgga cgagatggac      5460
tgccagggct gcggggagaa cagggccttc caggaccttc aggaccacct ggcctccctg      5520
gcaagcccgg ggaggatgga aagcccggcc tgaatggaaa aaacggggaa cccgggatc      5580
ctggggagga cggacgcaag ggggaaaagg gcgattccgg cgcctctggc agagagggca      5640
gggacggacc aaaaggggag gcgcggagcac ccggcattct gggtcctcag gggccacctg      5700
gattgccagg tccagttggt cctcctggcc aggggtttcc cggcgtccca ggcggtacag      5760
ggcctaaagg ggatagaggc gagacaggca gcaaagggga acaggggctc ccaggcgaaa      5820
ggggcttgag aggcgagcct ggctccgtgc ctaacgtgga cagactgctg gaaaccgccg      5880
gcatcaaggc ctccgccctg cgcgagatcg tggaaacctg ggacgagtcc tccggctcct      5940
tcctgcccgt gcctgagcgc agaagggggc cgaaagggga ctctggcgag caaggaccac      6000
ccggcaaaga gggacccatc ggcttccctg gggagcgggg gttgaaaggc gataggggag      6060
atccaggccc acaagggcct ccaggctgg cacttggaga gcgtggtcct ccaggaccaa      6120
gcggactggc aggggagccc ggaaagcctg gaatccccgg gttgcctggt agagccggcg      6180
gagtgggcga agcaggcagg cctggggaac gcggagagag aggcgaaaag gggcgaaagag      6240
gggagcaggg ccgcgacggt ccccccggac tacctggaac tccagggccc ccaggacccc      6300
ccggacctaa ggtgtccgtg gatgagcctg ccccggact gagcggagaa caaggtccac      6360
ctggcttgaa gggtgccaag ggggagccag gctctaacgg cgatcaaggg cccaaggggg      6420
atcggggagt gcctggcatc aaaggggacc ggggcgaacc cggtcctaga gggcaagacg      6480
gaaaccccgg cttgccgggc gaacgggaa tggctggtcc cgagggaaag ccaggcttgc      6540
agggacctag ggggcctccc ggtcctgtgg gtggacatgg cgatccgggt ccaccaggtg      6600
ctccaggact cgctggtcca gcaggccctc aggaccatc cggcctgaaa ggggaaccag      6660
gcgaaactgg ccccccaggc agaggcctga caggccctac tggtgctgtg ggcctccctg      6720
gacctcctgg ccctagtgga ctcgtgggcc ctcagggctc tcccggactg ccaggccaag      6780
tgggcgagac tggaaaaccc ggggctcccg gcagggatgg cgcttctgga aaagacggcg      6840
ataggggcag ccctggcgtg cccggtagtc cagggctacc tggccctgtg ggtccccaag      6900
gggagcctgg acctacaggc gcaccaggcc aggctgtagt ggggctgcct ggcgctaaag      6960
gcgagaaggg tgctcctggc ggcctggctg gcgatctcgt tggagaacct ggcgccaagg      7020
gcgaccgtgg cttgccagga cctcgcgcg agaaaggcga agctggcaga gctggcgagc      7080
```

```
ctggggaccc aggcgaagat ggccagaaag gcgctcccgg ccctaaggga ttcaagggcg      7140
atccggcgt gggcgtgcca ggctctccag gtcctcctgg accacccggt gtcaagggcg       7200
atttgggcct tcctggcctg ccaggggcac ctggcgtcgt gggctttcct ggacagaccg      7260
gcccacgggg agagatggga cagccaggcc ccagcggaga agagggctg gctggcccgc       7320
ctggcaggga aggcatacca ggcccattgg ggcctccagg cccacctgga tctgtggggc      7380
ctcctggcgc ctctggactg aaaggcgaca aaggcgatcc tggtgtcggc ctgccaggcc      7440
caagaggcga gaggggagag cccggcatca ggggcgaaga tggacggcct ggccaagagg      7500
gccctcgggg attgaccggc cctcctggat ccagaggcga acggggggag aaggggacg       7560
tgggctctgc tggcctcaaa ggcgacaagg gggactccgc cgtgattctg ggccctcccg      7620
gacctcgggg agctaagggg gacatgggag agagggtcc acggggactg gatgggaca        7680
agggaccacg cggagacaac ggcgacccgg gggataaggg ctccaagggc gaacctggcg      7740
ataagggatc cgctggactg cctggcctga ggggcctgct gggacctcaa ggacaaccag      7800
gcgccgcagg catccctggc gaccctggat ctcctggaaa ggacgcgtg cccggcatcc       7860
gcggagaaaa gggggatgtc ggcttcatgg gccccagggg gctgaagggg aaaggggag      7920
tgaagggcgc ttgcggcctc gatggggaaa aggggacaa gggggaggct ggccctccag       7980
gacgacctgg actggctggc cacaaggggcg aaatgggaga gccaggcgtg cccggacagt      8040
ccggcgctcc aggcaaagag ggcctgatcg gccccaaagg cgatagagga ttgacggcc       8100
agcctggccc aaagggcgat caaggcgaaa aggggagag aggcaccccc ggcatcggcg       8160
gctttccagg ccctctgga aacgatggct ctgccggccc acctgggcca cctggtagtg       8220
tgggaccaag aggccccgag ggactgcagg acagaaagg cgagagggg cccctggcg        8280
agagagttgt gggagcacct ggcgttcccg gcgcacccgg cgaaagggga gaacaaggca      8340
gacctggacc agccggaccc cgtggggaaa aaggcgaggc cgccctgacc gaggacgaca      8400
tcagaggctt cgtgcggcaa gagatgtccc agcactgcgc ctgtcaggcc cagttatcg       8460
cctccggcag cagacccctg ccttcctacg ctgccgatac cgccggctct cagctgcacg      8520
ctgtgcctgt gctccgggtg tcccacgccg aggaagagga aagagtccct cctgaggacg      8580
acgagtacag cgagtactct gagtattccg tggaagagta ccaggatccc gaggcccctt      8640
gggacagcga cgaccttgc tccctgcctc tggatgaggg ctcctgcacc gcctacaccc       8700
tgagatggta tcaccgggcc gtgacaggct ccaccgaggc ctgtcacccct ttcgtgtatg     8760
gcggctgcgg cggcaacgcc aatagattcg gcacccgcga ggcctgcgag cggagatgtc      8820
ctcccagagt ggtgcagtcc cagggcaccg gcacagccca ggactgatag tctagagtgg      8880
ccggcc                                                                8886
```

<210> SEQ ID NO 2
<211> LENGTH: 2944
<212> TYPE: PRT
<213> ORGANISM: Homo sapiens

<400> SEQUENCE: 2

Met Thr Leu Arg Leu Leu Val Ala Ala Leu Cys Ala Gly Ile Leu Ala
1               5                   10                  15

Glu Ala Pro Arg Val Arg Ala Gln His Arg Glu Arg Val Thr Cys Thr
                20                  25                  30

Arg Leu Tyr Ala Ala Asp Ile Val Phe Leu Leu Asp Gly Ser Ser Ser
            35                  40                  45

```
Ile Gly Arg Ser Asn Phe Arg Glu Val Arg Ser Phe Leu Glu Gly Leu
 50                  55                  60

Val Leu Pro Phe Ser Gly Ala Ala Ser Ala Gln Gly Val Arg Phe Ala
 65                  70                  75                  80

Thr Val Gln Tyr Ser Asp Asp Pro Arg Thr Glu Phe Gly Leu Asp Ala
                     85                  90                  95

Leu Gly Ser Gly Gly Asp Val Ile Arg Ala Ile Arg Glu Leu Ser Tyr
                100                 105                 110

Lys Gly Gly Asn Thr Arg Thr Gly Ala Ala Ile Leu His Val Ala Asp
                115                 120                 125

His Val Phe Leu Pro Gln Leu Ala Arg Pro Gly Val Pro Lys Val Cys
            130                 135                 140

Ile Leu Ile Thr Asp Gly Lys Ser Gln Asp Leu Val Asp Thr Ala Ala
145                 150                 155                 160

Gln Arg Leu Lys Gly Gln Gly Val Lys Leu Phe Ala Val Gly Ile Lys
                165                 170                 175

Asn Ala Asp Pro Glu Glu Leu Lys Arg Val Ala Ser Gln Pro Thr Ser
                180                 185                 190

Asp Phe Phe Phe Phe Val Asn Asp Phe Ser Ile Leu Arg Thr Leu Leu
            195                 200                 205

Pro Leu Val Ser Arg Arg Val Cys Thr Thr Ala Gly Gly Val Pro Val
210                 215                 220

Thr Arg Pro Pro Asp Asp Ser Thr Ser Ala Pro Arg Asp Leu Val Leu
225                 230                 235                 240

Ser Glu Pro Ser Ser Gln Ser Leu Arg Val Gln Trp Thr Ala Ala Ser
                245                 250                 255

Gly Pro Val Thr Gly Tyr Lys Val Gln Tyr Thr Pro Leu Thr Gly Leu
                260                 265                 270

Gly Gln Pro Leu Pro Ser Glu Arg Gln Glu Val Asn Val Pro Ala Gly
            275                 280                 285

Glu Thr Ser Val Arg Leu Arg Gly Leu Arg Pro Leu Thr Glu Tyr Gln
            290                 295                 300

Val Thr Val Ile Ala Leu Tyr Ala Asn Ser Ile Gly Glu Ala Val Ser
305                 310                 315                 320

Gly Thr Ala Arg Thr Thr Ala Leu Glu Gly Pro Glu Leu Thr Ile Gln
                325                 330                 335

Asn Thr Thr Ala His Ser Leu Leu Val Ala Trp Arg Ser Val Pro Gly
                340                 345                 350

Ala Thr Gly Tyr Arg Val Thr Trp Arg Val Leu Ser Gly Gly Pro Thr
            355                 360                 365

Gln Gln Gln Glu Leu Gly Pro Gly Gln Gly Ser Val Leu Leu Arg Asp
370                 375                 380

Leu Glu Pro Gly Thr Asp Tyr Glu Val Thr Val Ser Thr Leu Phe Gly
385                 390                 395                 400

Arg Ser Val Gly Pro Ala Thr Ser Leu Met Ala Arg Thr Asp Ala Ser
                405                 410                 415

Val Glu Gln Thr Leu Arg Pro Val Ile Leu Gly Pro Thr Ser Ile Leu
            420                 425                 430

Leu Ser Trp Asn Leu Val Pro Glu Ala Arg Gly Tyr Arg Leu Glu Trp
            435                 440                 445

Arg Arg Glu Thr Gly Leu Glu Pro Pro Gln Lys Val Val Leu Pro Ser
450                 455                 460

Asp Val Thr Arg Tyr Gln Leu Asp Gly Leu Gln Pro Gly Thr Glu Tyr
```

```
              465                 470                 475                 480
              Arg Leu Thr Leu Tyr Thr Leu Leu Glu Gly His Glu Val Ala Thr Pro
                              485                 490                 495
              Ala Thr Val Val Pro Thr Gly Pro Glu Leu Pro Val Ser Pro Val Thr
                              500                 505                 510
              Asp Leu Gln Ala Thr Glu Leu Pro Gly Gln Arg Val Arg Val Ser Trp
                              515                 520                 525
              Ser Pro Val Pro Gly Ala Thr Gln Tyr Arg Ile Ile Val Arg Ser Thr
                              530                 535                 540
              Gln Gly Val Glu Arg Thr Leu Val Leu Pro Gly Ser Gln Thr Ala Phe
              545                 550                 555                 560
              Asp Leu Asp Asp Val Gln Ala Gly Leu Ser Tyr Thr Val Arg Val Ser
                              565                 570                 575
              Ala Arg Val Gly Pro Arg Glu Gly Ser Ala Ser Val Leu Thr Val Arg
                              580                 585                 590
              Arg Glu Pro Glu Thr Pro Leu Ala Val Pro Gly Leu Arg Val Val Val
                              595                 600                 605
              Ser Asp Ala Thr Arg Val Arg Val Ala Trp Gly Pro Val Pro Gly Ala
                              610                 615                 620
              Ser Gly Phe Arg Ile Ser Trp Ser Thr Gly Ser Gly Pro Glu Ser Ser
              625                 630                 635                 640
              Gln Thr Leu Pro Pro Asp Ser Thr Ala Thr Asp Ile Thr Gly Leu Gln
                              645                 650                 655
              Pro Gly Thr Thr Tyr Gln Val Ala Val Ser Val Leu Arg Gly Arg Glu
                              660                 665                 670
              Glu Gly Pro Ala Ala Val Ile Val Ala Arg Thr Asp Pro Leu Gly Pro
                              675                 680                 685
              Val Arg Thr Val His Val Thr Gln Ala Ser Ser Ser Ser Val Thr Ile
                              690                 695                 700
              Thr Trp Thr Arg Val Pro Gly Ala Thr Gly Tyr Arg Val Ser Trp His
              705                 710                 715                 720
              Ser Ala His Gly Pro Glu Lys Ser Gln Leu Val Ser Gly Glu Ala Thr
                              725                 730                 735
              Val Ala Glu Leu Asp Gly Leu Glu Pro Asp Thr Glu Tyr Thr Val His
                              740                 745                 750
              Val Arg Ala His Val Ala Gly Val Asp Gly Pro Pro Ala Ser Val Val
                              755                 760                 765
              Val Arg Thr Ala Pro Glu Pro Val Gly Arg Val Ser Arg Leu Gln Ile
                              770                 775                 780
              Leu Asn Ala Ser Ser Asp Val Leu Arg Ile Thr Trp Val Gly Val Thr
              785                 790                 795                 800
              Gly Ala Thr Ala Tyr Arg Leu Ala Trp Gly Arg Ser Glu Gly Gly Pro
                              805                 810                 815
              Met Arg His Gln Ile Leu Pro Gly Asn Thr Asp Ser Ala Glu Ile Arg
                              820                 825                 830
              Gly Leu Glu Gly Gly Val Ser Tyr Ser Val Arg Val Thr Ala Leu Val
                              835                 840                 845
              Gly Asp Arg Glu Gly Thr Pro Val Ser Ile Val Val Thr Thr Pro Pro
                              850                 855                 860
              Glu Ala Pro Pro Ala Leu Gly Thr Leu His Val Val Gln Arg Gly Glu
              865                 870                 875                 880
              His Ser Leu Arg Leu Arg Trp Glu Pro Val Pro Arg Ala Gln Gly Phe
                              885                 890                 895
```

-continued

Leu Leu His Trp Gln Pro Glu Gly Gly Gln Glu Gln Ser Arg Val Leu
            900                 905                 910
Gly Pro Glu Leu Ser Ser Tyr His Leu Asp Gly Leu Glu Pro Ala Thr
        915                 920                 925
Gln Tyr Arg Val Arg Leu Ser Val Leu Gly Pro Ala Gly Glu Gly Pro
    930                 935                 940
Ser Ala Glu Val Thr Ala Arg Thr Glu Ser Pro Arg Val Pro Ser Ile
945                 950                 955                 960
Glu Leu Arg Val Val Asp Thr Ser Ile Asp Ser Val Thr Leu Ala Trp
                965                 970                 975
Thr Pro Val Ser Arg Ala Ser Ser Tyr Ile Leu Ser Trp Arg Pro Leu
            980                 985                 990
Arg Gly Pro Gly Gln Glu Val Pro Gly Ser Pro Gln Thr Leu Pro Gly
        995                 1000                1005
Ile Ser Ser Ser Gln Arg Val Thr Gly Leu Glu Pro Gly Val Ser
    1010                1015                1020
Tyr Ile Phe Ser Leu Thr Pro Val Leu Asp Gly Val Arg Gly Pro
    1025                1030                1035
Glu Ala Ser Val Thr Gln Thr Pro Val Cys Pro Arg Gly Leu Ala
    1040                1045                1050
Asp Val Val Phe Leu Pro His Ala Thr Gln Asp Asn Ala His Arg
    1055                1060                1065
Ala Glu Ala Thr Arg Arg Val Leu Glu Arg Leu Val Leu Ala Leu
    1070                1075                1080
Gly Pro Leu Gly Pro Gln Ala Val Gln Val Gly Leu Leu Ser Tyr
    1085                1090                1095
Ser His Arg Pro Ser Pro Leu Phe Pro Leu Asn Gly Ser His Asp
    1100                1105                1110
Leu Gly Ile Ile Leu Gln Arg Ile Arg Asp Met Pro Tyr Met Asp
    1115                1120                1125
Pro Ser Gly Asn Asn Leu Gly Thr Ala Val Val Thr Ala His Arg
    1130                1135                1140
Tyr Met Leu Ala Pro Asp Ala Pro Gly Arg Arg Gln His Val Pro
    1145                1150                1155
Gly Val Met Val Leu Leu Val Asp Glu Pro Leu Arg Gly Asp Ile
    1160                1165                1170
Phe Ser Pro Ile Arg Glu Ala Gln Ala Ser Gly Leu Asn Val Val
    1175                1180                1185
Met Leu Gly Met Ala Gly Ala Asp Pro Glu Gln Leu Arg Arg Leu
    1190                1195                1200
Ala Pro Gly Met Asp Ser Val Gln Thr Phe Phe Ala Val Asp Asp
    1205                1210                1215
Gly Pro Ser Leu Asp Gln Ala Val Ser Gly Leu Ala Thr Ala Leu
    1220                1225                1230
Cys Gln Ala Ser Phe Thr Thr Gln Pro Arg Pro Glu Pro Cys Pro
    1235                1240                1245
Val Tyr Cys Pro Lys Gly Gln Lys Gly Glu Pro Gly Glu Met Gly
    1250                1255                1260
Leu Arg Gly Gln Val Gly Pro Pro Gly Asp Pro Gly Leu Pro Gly
    1265                1270                1275
Arg Thr Gly Ala Pro Gly Pro Gln Gly Pro Pro Gly Ser Ala Thr
    1280                1285                1290

```
Ala Lys Gly Glu Arg Gly Phe Pro Gly Ala Asp Gly Arg Pro Gly
    1295                1300                1305

Ser Pro Gly Arg Ala Gly Asn Pro Gly Thr Pro Gly Ala Pro Gly
    1310                1315                1320

Leu Lys Gly Ser Pro Gly Leu Pro Gly Pro Arg Gly Asp Pro Gly
    1325                1330                1335

Glu Arg Gly Pro Arg Gly Pro Lys Gly Glu Pro Gly Ala Pro Gly
    1340                1345                1350

Gln Val Ile Gly Glu Gly Pro Gly Leu Pro Gly Arg Lys Gly
    1355                1360                1365

Asp Pro Gly Pro Ser Gly Pro Gly Pro Arg Gly Pro Leu Gly
    1370                1375                1380

Asp Pro Gly Pro Arg Gly Pro Gly Leu Pro Gly Thr Ala Met
    1385                1390                1395

Lys Gly Asp Lys Gly Asp Arg Gly Glu Arg Gly Pro Pro Gly Pro
    1400                1405                1410

Gly Glu Gly Gly Ile Ala Pro Gly Glu Pro Gly Leu Pro Gly Leu
    1415                1420                1425

Pro Gly Ser Pro Gly Pro Gln Gly Pro Val Gly Pro Pro Gly Lys
    1430                1435                1440

Lys Gly Glu Lys Gly Asp Ser Glu Asp Gly Ala Pro Gly Leu Pro
    1445                1450                1455

Gly Gln Pro Gly Ser Pro Gly Glu Gln Gly Pro Arg Gly Pro Pro
    1460                1465                1470

Gly Ala Ile Gly Pro Lys Gly Asp Arg Gly Phe Pro Gly Pro Leu
    1475                1480                1485

Gly Glu Ala Gly Glu Lys Gly Glu Arg Gly Pro Pro Gly Pro Ala
    1490                1495                1500

Gly Ser Arg Gly Leu Pro Gly Val Ala Gly Arg Pro Gly Ala Lys
    1505                1510                1515

Gly Pro Glu Gly Pro Pro Gly Pro Thr Gly Arg Gln Gly Glu Lys
    1520                1525                1530

Gly Glu Pro Gly Arg Pro Gly Asp Pro Ala Val Val Gly Pro Ala
    1535                1540                1545

Val Ala Gly Pro Lys Gly Glu Lys Gly Asp Val Gly Pro Ala Gly
    1550                1555                1560

Pro Arg Gly Ala Thr Gly Val Gln Gly Glu Arg Gly Pro Pro Gly
    1565                1570                1575

Leu Val Leu Pro Gly Asp Pro Gly Pro Lys Gly Asp Pro Gly Asp
    1580                1585                1590

Arg Gly Pro Ile Gly Leu Thr Gly Arg Ala Gly Pro Pro Gly Asp
    1595                1600                1605

Ser Gly Pro Pro Gly Glu Lys Gly Asp Pro Gly Arg Pro Gly Pro
    1610                1615                1620

Pro Gly Pro Val Gly Pro Arg Gly Arg Asp Gly Glu Val Gly Glu
    1625                1630                1635

Lys Gly Asp Glu Gly Pro Pro Gly Asp Pro Gly Leu Pro Gly Lys
    1640                1645                1650

Ala Gly Glu Arg Gly Leu Arg Gly Ala Pro Gly Val Arg Gly Pro
    1655                1660                1665

Val Gly Glu Lys Gly Asp Gln Gly Asp Pro Gly Glu Asp Gly Arg
    1670                1675                1680

Asn Gly Ser Pro Gly Ser Ser Gly Pro Lys Gly Asp Arg Gly Glu
```

-continued

```
            1685                1690                1695
Pro Gly Pro Pro Gly Pro Pro Gly Arg Leu Val Asp Thr Gly Pro
        1700                1705                1710
Gly Ala Arg Glu Lys Gly Glu Pro Gly Asp Arg Gly Gln Glu Gly
        1715                1720                1725
Pro Arg Gly Pro Lys Gly Asp Pro Gly Leu Pro Gly Ala Pro Gly
        1730                1735                1740
Glu Arg Gly Ile Glu Gly Phe Arg Gly Pro Pro Gly Pro Gln Gly
        1745                1750                1755
Asp Pro Gly Val Arg Gly Pro Ala Gly Glu Lys Gly Asp Arg Gly
        1760                1765                1770
Pro Pro Gly Leu Asp Gly Arg Ser Gly Leu Asp Gly Lys Pro Gly
        1775                1780                1785
Ala Ala Gly Pro Ser Gly Pro Asn Gly Ala Ala Gly Lys Ala Gly
        1790                1795                1800
Asp Pro Gly Arg Asp Gly Leu Pro Gly Leu Arg Gly Glu Gln Gly
        1805                1810                1815
Leu Pro Gly Pro Ser Gly Pro Pro Gly Leu Pro Gly Lys Pro Gly
        1820                1825                1830
Glu Asp Gly Lys Pro Gly Leu Asn Gly Lys Asn Gly Glu Pro Gly
        1835                1840                1845
Asp Pro Gly Glu Asp Gly Arg Lys Gly Glu Lys Gly Asp Ser Gly
        1850                1855                1860
Ala Ser Gly Arg Glu Gly Arg Asp Gly Pro Lys Gly Glu Arg Gly
        1865                1870                1875
Ala Pro Gly Ile Leu Gly Pro Gln Gly Pro Pro Gly Leu Pro Gly
        1880                1885                1890
Pro Val Gly Pro Pro Gly Gln Gly Phe Pro Gly Val Pro Gly Gly
        1895                1900                1905
Thr Gly Pro Lys Gly Asp Arg Gly Glu Thr Gly Ser Lys Gly Glu
        1910                1915                1920
Gln Gly Leu Pro Gly Glu Arg Gly Leu Arg Gly Glu Pro Gly Ser
        1925                1930                1935
Val Pro Asn Val Asp Arg Leu Leu Glu Thr Ala Gly Ile Lys Ala
        1940                1945                1950
Ser Ala Leu Arg Glu Ile Val Glu Thr Trp Asp Glu Ser Ser Gly
        1955                1960                1965
Ser Phe Leu Pro Val Pro Glu Arg Arg Arg Gly Pro Lys Gly Asp
        1970                1975                1980
Ser Gly Glu Gln Gly Pro Pro Gly Lys Glu Gly Pro Ile Gly Phe
        1985                1990                1995
Pro Gly Glu Arg Gly Leu Lys Gly Asp Arg Gly Asp Pro Gly Pro
        2000                2005                2010
Gln Gly Pro Pro Gly Leu Ala Leu Gly Glu Arg Gly Pro Pro Gly
        2015                2020                2025
Pro Ser Gly Leu Ala Gly Glu Pro Gly Lys Pro Gly Ile Pro Gly
        2030                2035                2040
Leu Pro Gly Arg Ala Gly Gly Val Gly Glu Ala Gly Arg Pro Gly
        2045                2050                2055
Glu Arg Gly Glu Arg Gly Glu Lys Gly Glu Arg Gly Glu Gln Gly
        2060                2065                2070
Arg Asp Gly Pro Pro Gly Leu Pro Gly Thr Pro Gly Pro Pro Gly
        2075                2080                2085
```

```
Pro Pro Gly Pro Lys Val Ser Val Asp Glu Pro Gly Pro Gly Leu
        2090                2095                2100
Ser Gly Glu Gln Gly Pro Pro Gly Leu Lys Gly Ala Lys Gly Glu
        2105                2110                2115
Pro Gly Ser Asn Gly Asp Gln Gly Pro Lys Gly Asp Arg Gly Val
        2120                2125                2130
Pro Gly Ile Lys Gly Asp Arg Gly Glu Pro Gly Pro Arg Gly Gln
        2135                2140                2145
Asp Gly Asn Pro Gly Leu Pro Gly Glu Arg Gly Met Ala Gly Pro
        2150                2155                2160
Glu Gly Lys Pro Gly Leu Gln Gly Pro Arg Gly Pro Pro Gly Pro
        2165                2170                2175
Val Gly Gly His Gly Asp Pro Gly Pro Pro Gly Ala Pro Gly Leu
        2180                2185                2190
Ala Gly Pro Ala Gly Pro Gln Gly Pro Ser Gly Leu Lys Gly Glu
        2195                2200                2205
Pro Gly Glu Thr Gly Pro Pro Gly Arg Gly Leu Thr Gly Pro Thr
        2210                2215                2220
Gly Ala Val Gly Leu Pro Gly Pro Pro Gly Pro Ser Gly Leu Val
        2225                2230                2235
Gly Pro Gln Gly Ser Pro Gly Leu Pro Gly Gln Val Gly Glu Thr
        2240                2245                2250
Gly Lys Pro Gly Ala Pro Gly Arg Asp Gly Ala Ser Gly Lys Asp
        2255                2260                2265
Gly Asp Arg Gly Ser Pro Gly Val Pro Gly Ser Pro Gly Leu Pro
        2270                2275                2280
Gly Pro Val Gly Pro Lys Gly Glu Pro Gly Pro Thr Gly Ala Pro
        2285                2290                2295
Gly Gln Ala Val Val Gly Leu Pro Gly Ala Lys Gly Glu Lys Gly
        2300                2305                2310
Ala Pro Gly Gly Leu Ala Gly Asp Leu Val Gly Glu Pro Gly Ala
        2315                2320                2325
Lys Gly Asp Arg Gly Leu Pro Gly Pro Arg Gly Glu Lys Gly Glu
        2330                2335                2340
Ala Gly Arg Ala Gly Glu Pro Gly Asp Pro Gly Glu Asp Gly Gln
        2345                2350                2355
Lys Gly Ala Pro Gly Pro Lys Gly Phe Lys Gly Asp Pro Gly Val
        2360                2365                2370
Gly Val Pro Gly Ser Pro Gly Pro Pro Gly Pro Pro Gly Val Lys
        2375                2380                2385
Gly Asp Leu Gly Leu Pro Gly Leu Pro Gly Ala Pro Gly Val Val
        2390                2395                2400
Gly Phe Pro Gly Gln Thr Gly Pro Arg Gly Glu Met Gly Gln Pro
        2405                2410                2415
Gly Pro Ser Gly Glu Arg Gly Leu Ala Gly Pro Pro Gly Arg Glu
        2420                2425                2430
Gly Ile Pro Gly Pro Leu Gly Pro Pro Gly Pro Pro Gly Ser Val
        2435                2440                2445
Gly Pro Pro Gly Ala Ser Gly Leu Lys Gly Asp Lys Gly Asp Pro
        2450                2455                2460
Gly Val Gly Leu Pro Gly Pro Arg Gly Glu Arg Gly Glu Pro Gly
        2465                2470                2475
```

-continued

```
Ile Arg Gly Glu Asp Gly Arg Pro Gly Gln Glu Gly Pro Arg Gly
2480                2485                2490

Leu Thr Gly Pro Pro Gly Ser Arg Gly Glu Arg Gly Glu Lys Gly
2495                2500                2505

Asp Val Gly Ser Ala Gly Leu Lys Gly Asp Lys Gly Asp Ser Ala
2510                2515                2520

Val Ile Leu Gly Pro Pro Gly Pro Arg Gly Ala Lys Gly Asp Met
2525                2530                2535

Gly Glu Arg Gly Pro Arg Gly Leu Asp Gly Asp Lys Gly Pro Arg
2540                2545                2550

Gly Asp Asn Gly Asp Pro Gly Asp Lys Gly Ser Lys Gly Glu Pro
2555                2560                2565

Gly Asp Lys Gly Ser Ala Gly Leu Pro Gly Leu Arg Gly Leu Leu
2570                2575                2580

Gly Pro Gln Gly Gln Pro Gly Ala Ala Gly Ile Pro Gly Asp Pro
2585                2590                2595

Gly Ser Pro Gly Lys Asp Gly Val Pro Gly Ile Arg Gly Glu Lys
2600                2605                2610

Gly Asp Val Gly Phe Met Gly Pro Arg Gly Leu Lys Gly Glu Arg
2615                2620                2625

Gly Val Lys Gly Ala Cys Gly Leu Asp Gly Glu Lys Gly Asp Lys
2630                2635                2640

Gly Glu Ala Gly Pro Pro Gly Arg Pro Gly Leu Ala Gly His Lys
2645                2650                2655

Gly Glu Met Gly Glu Pro Gly Val Pro Gly Gln Ser Gly Ala Pro
2660                2665                2670

Gly Lys Glu Gly Leu Ile Gly Pro Lys Gly Asp Arg Gly Phe Asp
2675                2680                2685

Gly Gln Pro Gly Pro Lys Gly Asp Gln Gly Glu Lys Gly Glu Arg
2690                2695                2700

Gly Thr Pro Gly Ile Gly Gly Phe Pro Gly Pro Ser Gly Asn Asp
2705                2710                2715

Gly Ser Ala Gly Pro Pro Gly Pro Pro Gly Ser Val Gly Pro Arg
2720                2725                2730

Gly Pro Glu Gly Leu Gln Gly Gln Lys Gly Glu Arg Gly Pro Pro
2735                2740                2745

Gly Glu Arg Val Val Gly Ala Pro Gly Val Pro Gly Ala Pro Gly
2750                2755                2760

Glu Arg Gly Glu Gln Gly Arg Pro Gly Pro Ala Gly Pro Arg Gly
2765                2770                2775

Glu Lys Gly Glu Ala Ala Leu Thr Glu Asp Asp Ile Arg Gly Phe
2780                2785                2790

Val Arg Gln Glu Met Ser Gln His Cys Ala Cys Gln Gly Gln Phe
2795                2800                2805

Ile Ala Ser Gly Ser Arg Pro Leu Pro Ser Tyr Ala Ala Asp Thr
2810                2815                2820

Ala Gly Ser Gln Leu His Ala Val Pro Val Leu Arg Val Ser His
2825                2830                2835

Ala Glu Glu Glu Glu Arg Val Pro Pro Glu Asp Asp Glu Tyr Ser
2840                2845                2850

Glu Tyr Ser Glu Tyr Ser Val Glu Glu Tyr Gln Asp Pro Glu Ala
2855                2860                2865

Pro Trp Asp Ser Asp Asp Pro Cys Ser Leu Pro Leu Asp Glu Gly
```

| | | | | | | | | | | | |
|---|---|---|---|---|---|---|---|---|---|---|---|
| | | | 2870 | | | 2875 | | | 2880 | | |
| Ser | Cys | Thr | Ala | Tyr | Thr | Leu | Arg | Trp | Tyr | His | Arg | Ala | Val | Thr |
| | | 2885 | | | | 2890 | | | | 2895 | |
| Gly | Ser | Thr | Glu | Ala | Cys | His | Pro | Phe | Val | Tyr | Gly | Gly | Cys | Gly |
| | 2900 | | | | 2905 | | | | 2910 | | |
| Gly | Asn | Ala | Asn | Arg | Phe | Gly | Thr | Arg | Glu | Ala | Cys | Glu | Arg | Arg |
| 2915 | | | | 2920 | | | | 2925 | | | |
| Cys | Pro | Pro | Arg | Val | Val | Gln | Ser | Gln | Gly | Thr | Gly | Thr | Ala | Gln |
| 2930 | | | | 2935 | | | | 2940 | | | |
| Asp |

<210> SEQ ID NO 3
<211> LENGTH: 1888
<212> TYPE: DNA
<213> ORGANISM: Homo sapiens

<400> SEQUENCE: 3

```
ccggtgccgg gcgaacatgg cggcggccac cggaccctcg ttttggctgg ggaatgaaac     60
cctgaaggtg ccgctggcgc tctttgcctt gaaccggcag cgcctgtgtg agcggctgcg    120
gaagaaccct gctgtgcagg ccggctccat cgtggtcctg cagggcgggg aggagactca    180
gcgctactgc accgacaccg ggtcctcttc ctccaggag tccttctttc actgggcgtt    240
cggtgtcact gagccaggct gctatggtgt catcgatgtt gacactggga agtcgaccct    300
gttttgtgccc aggcttcctg ccagccatgc cacctggatg ggaaagatcc attccaagga    360
gcacttcaag gagaagtatg ccgtggacga cgtccagtac gtagatgaga ttgccagcgt    420
cctgacgtca cagaagccct ctgtcctcct cactttgcgt ggcgtcaaca cggacagcgg    480
cagtgtctgc agggaggcct cctttgacgg catcagcaag ttcgaagtca caataccat    540
tcttcaccca gagatcgttg agagccgagt gtttaagacg gatatggagc tggaggttct    600
gcgctatacc aataaaatct ccagcgaggc caccgtgag gtaatgaagg ctgtaaaagt    660
gggaatgaaa gaatatgggt tggaaagcct cttcgagcac tactgctact cccggggcgg    720
catgcgccac agctcctaca cctgcatctg cggcagtggt gagaactcag ccgtgctaca    780
ctacggacac gccggagctc ccaacgaccg aacgatccag aatggggata tgtgcctgtt    840
cgacatgggc ggtgagtatt actctgtcgc ttccgacatc acctgctcct ttccccgcaa    900
cggcaagttc actgcagacc agaaggccgt ctatgaggca gtgctgctga gctcccgtgc    960
cgtcatgggt gccatgaagc caggtgactg gtggcctgac atcgaccgcc tggctgaccg   1020
catccacctg gaggagctgg cccacatggg catcctgagc ggcagcgtgg acgccatggt   1080
ccaggctcac ctgggggccg tgtttatgcc tcacgggctt ggccacttcc tgggcattga   1140
cgtgcacgac gtgggaggct acccagaggg cgtggagcgc atcgacgagc ccggcctgcg   1200
gagcctgcgc actgcacggc acctgcagcc aggcatggtg ctcaccgtgg agccgggcat   1260
ctacttcatc gaccacctcc tggatgaggc cctggcggac ccggcccgcg cctccttcct   1320
taaccgcgag gtcctgcagc gctttcgcgg ttttggcggg gtccgcatcg aggaggacgt   1380
cgtggtgatc gacagcggca tagagctgct gacctgcgtg ccccgcactg tggaagagat   1440
tgaagcatgc atggcaggct gtgacaaggc ctttaccccc ttctctggcc ccaagtagag   1500
ccagccagaa atcccagcgc acctgggggc ctggccttgc aacctctttt cgtgatgggc   1560
agcctgctgg tcagcactcc agtagcgaga cggcaccc agaatcagat ccagccttcg   1620
gcatttgatc agaccaaaca gtgctgtttc ccggggagga aacacttttt taattaccct   1680
```

```
tttgcaggca ccacctttaa tctgttttat accttgctta ttaaatgagc gacttaaaat   1740
gattgaaaat aatgctgtcc tttagtagca agtaaaatgt gtcttgctgt catttatatt   1800
ccttttccca ggaaagaagc atttctgata ctttctgtca aaaatcaata tgcagaatgg   1860
catttgcaat aaaaggtttc ctaaaatg                                      1888
```

<210> SEQ ID NO 4
<211> LENGTH: 486
<212> TYPE: PRT
<213> ORGANISM: Homo sapiens

<400> SEQUENCE: 4

```
Met Ala Ala Ala Thr Gly Pro Ser Phe Trp Leu Gly Asn Glu Thr Leu
1               5                   10                  15

Lys Val Pro Leu Ala Leu Phe Ala Leu Asn Arg Gln Arg Leu Cys Glu
            20                  25                  30

Arg Leu Arg Lys Asn Pro Ala Val Gln Ala Gly Ser Ile Val Val Leu
        35                  40                  45

Gln Gly Gly Glu Glu Thr Gln Arg Tyr Cys Thr Asp Thr Gly Val Leu
    50                  55                  60

Phe Arg Gln Glu Ser Phe Phe His Trp Ala Phe Gly Val Thr Glu Pro
65                  70                  75                  80

Gly Cys Tyr Gly Val Ile Asp Val Asp Thr Gly Lys Ser Thr Leu Phe
                85                  90                  95

Val Pro Arg Leu Pro Ala Ser His Ala Thr Trp Met Gly Lys Ile His
            100                 105                 110

Ser Lys Glu His Phe Lys Glu Lys Tyr Ala Val Asp Asp Val Gln Asp
        115                 120                 125

Glu Ile Ala Ser Val Leu Thr Ser Gln Lys Pro Ser Val Leu Leu Thr
    130                 135                 140

Leu Arg Gly Val Asn Thr Asp Ser Gly Ser Val Cys Arg Glu Ala Ser
145                 150                 155                 160

Phe Asp Gly Ile Ser Lys Phe Glu Val Asn Asn Thr Ile Leu His Pro
                165                 170                 175

Glu Ile Val Glu Cys Arg Val Phe Lys Thr Asp Met Glu Leu Glu Val
            180                 185                 190

Leu Arg Tyr Thr Asn Lys Ile Ser Ser Glu Ala His Arg Glu Val Met
        195                 200                 205

Lys Ala Val Lys Val Gly Met Lys Glu Tyr Glu Leu Glu Ser Leu Phe
    210                 215                 220

Glu His Tyr Cys Tyr Ser Arg Gly Gly Met Arg His Ser Ser Tyr Thr
225                 230                 235                 240

Cys Ile Cys Gly Ser Gly Glu Asn Ser Ala Val Leu His Gly Ala Gly
                245                 250                 255

Ala Pro Asn Asp Arg Thr Ile Gln Asn Gly Met Cys Leu Phe Asp Met
            260                 265                 270

Gly Gly Glu Tyr Tyr Cys Phe Ala Ser Asp Ile Thr Cys Ser Phe Pro
        275                 280                 285

Ala Asn Gly Lys Phe Thr Ala Asp Gln Lys Ala Val Tyr Glu Ala Val
    290                 295                 300

Leu Arg Ser Ser Arg Ala Val Met Gly Ala Met Lys Pro Gly Val Trp
305                 310                 315                 320

Trp Pro Asp Met His Arg Leu Ala Asp Arg Ile His Leu Glu Glu Leu
                325                 330                 335
```

```
Ala His Met Gly Ile Leu Ser Gly Ser Val Asp Ala Met Val Gln Ala
            340                 345                 350

His Leu Gly Ala Val Phe Met Pro His Gly Leu Gly His Phe Leu Gly
            355                 360                 365

Ile Asp Val His Asp Val Gly Gly Tyr Pro Gly Val Arg Ile Asp Glu
            370                 375                 380

Pro Gly Leu Arg Ser Leu Arg Thr Ala Arg His Leu Gln Pro Gly Met
385                 390                 395                 400

Val Leu Thr Val Glu Pro Gly Ile Tyr Phe Ile Asp His Leu Leu Asp
            405                 410                 415

Glu Ala Leu Ala Asp Pro Ala Arg Ala Ser Phe Leu Asn Arg Glu Val
            420                 425                 430

Leu Gln Arg Phe Arg Gly Phe Gly Gly Val Arg Ile Glu Glu Asp Val
            435                 440                 445

Val Val Thr Asp Ser Gly Ile Glu Leu Leu Thr Cys Val Pro Arg Thr
            450                 455                 460

Val Glu Glu Ile Glu Ala Cys Met Ala Gly Cys Asp Lys Ala Phe Thr
465                 470                 475                 480

Pro Phe Ser Gly Pro Lys
            485

<210> SEQ ID NO 5
<211> LENGTH: 397
<212> TYPE: PRT
<213> ORGANISM: Rattus norvegicus

<400> SEQUENCE: 5

Met Ile His Thr Asn Leu Lys Lys Phe Ser Leu Phe Ile Leu Val
1               5                   10                  15

Phe Leu Leu Phe Ala Val Ile Cys Val Trp Lys Lys Gly Ser Asp Tyr
            20                  25                  30

Glu Ala Leu Thr Leu Gln Ala Lys Glu Phe Gln Met Pro Lys Ser Gln
            35                  40                  45

Glu Lys Val Ala Met Gly Ser Ala Ser Gln Val Val Phe Ser Asn Ser
50                  55                  60

Lys Gln Asp Pro Lys Glu Asp Ile Pro Ile Leu Ser Tyr His Arg Val
65                  70                  75                  80

Thr Ala Lys Val Lys Pro Gln Pro Ser Phe Gln Val Trp Asp Lys Asp
            85                  90                  95

Ser Thr Tyr Ser Lys Leu Asn Pro Arg Leu Leu Lys Ile Trp Arg Asn
            100                 105                 110

Tyr Leu Asn Met Asn Lys Tyr Lys Val Ser Tyr Lys Gly Pro Gly Val
            115                 120                 125

Lys Phe Ser Val Glu Ala Leu Arg Cys His Leu Arg Asp His Val Asn
            130                 135                 140

Val Ser Met Ile Glu Ala Thr Asp Phe Pro Phe Asn Thr Thr Glu Trp
145                 150                 155                 160

Glu Gly Tyr Leu Pro Lys Glu Asn Phe Arg Thr Lys Val Gly Pro Trp
            165                 170                 175

Gln Arg Cys Ala Val Val Ser Ser Ala Gly Ser Leu Lys Asn Ser Gln
            180                 185                 190

Leu Gly Arg Glu Ile Asp Asn His Asp Ala Val Leu Arg Phe Asn Gly
            195                 200                 205

Ala Pro Thr Asp Asn Phe Gln Gln Asp Val Gly Ser Lys Thr Thr Ile
```

```
                210               215               220
Arg Leu Met Asn Ser Gln Leu Val Thr Thr Glu Lys Arg Phe Leu Lys
225                 230                 235                 240

Asp Ser Leu Tyr Thr Glu Gly Ile Leu Ile Val Trp Asp Ser Tyr His
                245                 250                 255

Ala Asp Ile Pro Lys Trp Tyr Gln Pro Asp Tyr Asn Phe Phe Glu
                260                 265                 270

Thr Tyr Lys Ser Tyr Arg Arg Leu Asn Pro Ser Gln Pro Phe Tyr Ile
                275                 280                 285

Leu Lys Pro Gln Met Pro Trp Glu Leu Trp Asp Ile Ile Gln Glu Ile
                290                 295                 300

Ser Ala Asp Leu Ile Gln Pro Asn Pro Pro Ser Ser Gly Met Leu Gly
305                 310                 315                 320

Ile Ile Ile Met Met Thr Leu Cys Asp Gln Val Asp Ile Tyr Glu Phe
                325                 330                 335

Leu Pro Ser Lys Arg Lys Thr Asp Val Cys Tyr Tyr His Gln Lys Phe
                340                 345                 350

Phe Asp Ser Ala Cys Thr Met Gly Ala Tyr His Pro Leu Leu Phe Glu
                355                 360                 365

Lys Asn Met Val Lys His Leu Asn Glu Gly Thr Glu Asp Tyr Leu Phe
                370                 375                 380

Gly Lys Ala Thr Leu Ser Gly Phe Arg Asn Ile Arg Cys
385                 390                 395

<210> SEQ ID NO 6
<211> LENGTH: 247
<212> TYPE: PRT
<213> ORGANISM: Homo sapiens

<400> SEQUENCE: 6

Met Ala His His His His His His Leu Pro Ala Leu Lys Leu Ala Leu
1               5                   10                  15

Glu Tyr Ile Val Pro Cys Met Asn Lys His Gly Ile Cys Val Val Asp
                20                  25                  30

Asp Phe Leu Gly Lys Glu Thr Gly Gln Gln Ile Gly Asp Glu Val Arg
            35                  40                  45

Ala Leu His Asp Thr Gly Lys Phe Thr Asp Gly Gln Leu Val Ser Gln
        50                  55                  60

Lys Ser Asp Ser Ser Lys Asp Ile Arg Gly Asp Lys Ile Thr Trp Ile
65                  70                  75                  80

Glu Gly Lys Glu Pro Gly Cys Glu Thr Ile Gly Leu Leu Met Ser Ser
                85                  90                  95

Met Asp Asp Leu Ile Arg His Cys Asn Gly Lys Leu Gly Ser Tyr Lys
                100                 105                 110

Ile Asn Gly Arg Thr Lys Ala Met Val Ala Cys Tyr Pro Gly Asn Gly
            115                 120                 125

Thr Gly Tyr Val Arg His Val Asp Asn Pro Asn Gly Asp Gly Arg Cys
        130                 135                 140

Val Thr Cys Ile Tyr Tyr Leu Asn Lys Asp Trp Asp Ala Lys Val Ser
145                 150                 155                 160

Gly Gly Ile Leu Arg Ile Phe Pro Glu Gly Lys Ala Gln Phe Ala Asp
                165                 170                 175

Ile Glu Pro Lys Phe Asp Arg Leu Leu Phe Phe Trp Ser Asp Arg Arg
                180                 185                 190
```

```
Asn Pro His Glu Val Gln Pro Ala Tyr Ala Thr Arg Tyr Ala Ile Thr
        195                 200                 205
Val Trp Tyr Phe Asp Ala Asp Glu Arg Ala Arg Ala Lys Val Lys Tyr
    210                 215                 220
Leu Thr Gly Glu Lys Gly Val Arg Val Glu Leu Asn Lys Pro Ser Asp
225                 230                 235                 240
Ser Val Gly Lys Asp Val Phe
                245
```